(12) United States Patent
Ascher et al.

(10) Patent No.: US 6,440,957 B1
(45) Date of Patent: Aug. 27, 2002

(54) CEPHALOSPORINES HAVING CYCLIC AMINOGUANIDINE SUBSTITUENTS AS ANTIBIOTICS

(75) Inventors: Gerd Ascher, Kundl; Werner Heilmayer, Mödling; Johannes Ludescher, Breitenbach; Johannes Hildebrandt, Oeynhausen; Michael Schranz, Vienna; Josef Wieser, Polling, all of (AT)

(73) Assignee: Biochemie Gesellschaft m.b.H., Kundl (AT)

( * ) Notice: Subject to any disclaimer, the term of this patent is extended or adjusted under 35 U.S.C. 154(b) by 0 days.

(21) Appl. No.: 09/667,075

(22) Filed: Sep. 21, 2000

(30) Foreign Application Priority Data

Mar. 23, 1998 (AT) ............................................. A 515/98

(51) Int. Cl.[7] ...................... C07D 401/46; A61K 31/546

(52) U.S. Cl. ........................ 514/205; 514/206; 540/222

(58) Field of Search ......................... 540/222; 514/205, 514/206

(56) References Cited

FOREIGN PATENT DOCUMENTS

| EP | 0 164 944 | 7/1990 |
|----|-----------|--------|
| WO | WO 96/35692 | 11/1996 |
| WO | WO 98/43981 | 10/1998 |

OTHER PUBLICATIONS

Huenig et al., Justus Liebigs Ann. Chem., vol. 651, pp. 89–101 (1962).
Quadri et al., J. Med. Chem., vol. 39, pp. 3385–3393 (1996).
Chemical Abstracts 16306 Di(guanylhydrazones), Meiser et al., DE 943, 408, May 17, 1956.
International Search Report.

*Primary Examiner*—Mark Berch
(74) *Attorney, Agent, or Firm*—Hesna J. Pfeiffer

(57) ABSTRACT

A compound useful as an anti-bacterial agent, having the formula

I

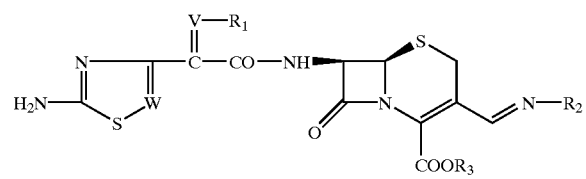

wherein $R_2$ together with the nitrogen atom to which it is attached forms a cyclic aminoguanidine group or derivative thereof as defined

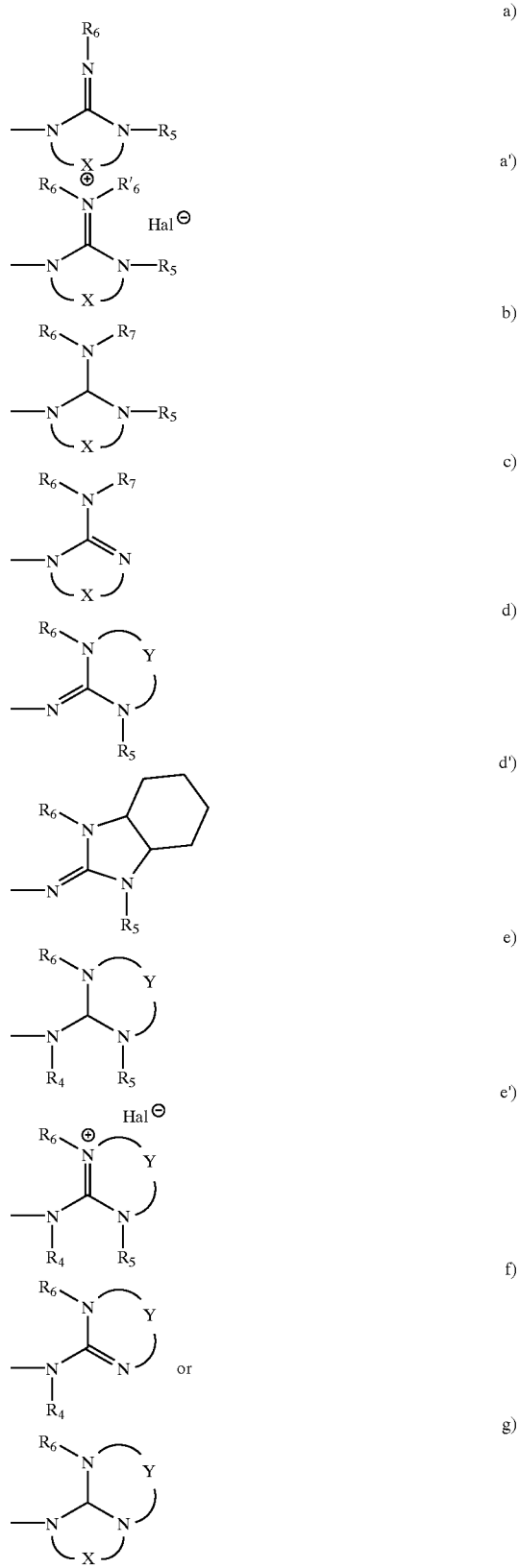

8 Claims, No Drawings

CEPHALOSPORINES HAVING CYCLIC AMINOGUANIDINE SUBSTITUENTS AS ANTIBIOTICS

This is a continuation of PCT/EP99/01853 filed Mar. 19, 1999.

The present invention relates to antibacterial compounds which are 7-acylamino-3-(cyclic aminoguanidine) methylene cephalosporins, including 3-cyclic aminoguanidine-like structured compounds having a triamino-methylidyne group instead of an aminoguanidine group.

In one aspect the present invention provides a compound of formula

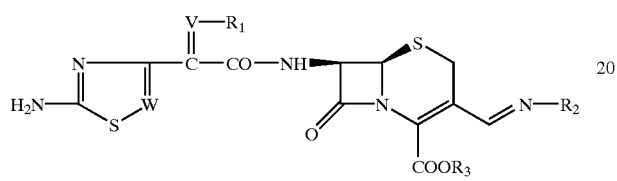

I wherein
W denotes CH or N,
V denotes CH or NO,
$R_1$ denotes hydrogen, acyl, carboxyl or alkyl,
$R_3$ denotes hydrogen or an ester moiety,
$R_2$ denotes a group of formula

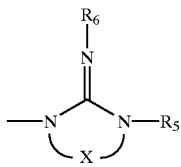

a)

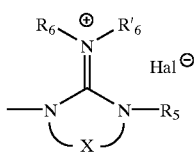

a')

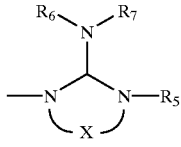

b)

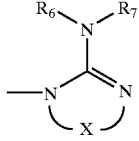

c)

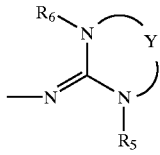

d)

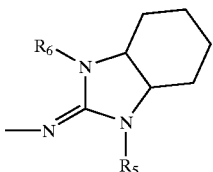

d')

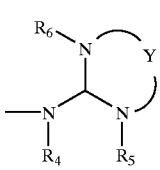

e)

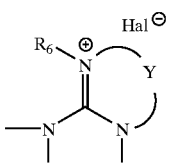

e')

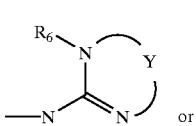

f)

g)

wherein
X and Y independently of each other each denote $(C_{2-5})$alkylene, or $(C_{2-5})$alkenylene wherein one —C=C— double bond is present, or, in case of at least $C_4$-alkenylene, wherein two —C=C— double bonds are present,
$R_4$ denotes hydrogen or alkyl,
$R_5$ denotes hydrogen, alkyl, or aminoiminomethyl,
$R_6$ denotes hydrogen, alkyl, cycloalkyl, amino, hydroxy, alkoxy, heterocyclyl or a group of formula —N=CHR$_8$, wherein
$R_8$ denotes alkyl, aryl or heterocyclyl, or
$R_5$ and $R_6$ together with the nitrogen atoms to which they are attached denote heterocyclyl,
$R'_6$ denotes alkyl,
$R_7$ denotes hydrogen, or
$R_6$ and $R_7$ together with the nitrogen atom to which they are attached form heterocyclyl.

In formula I $R_3$ is hydrogen or an ester moiety.

An ester moiety includes alkyl; e.g. unsubstituted alkyl or substituted alkyl, e.g. by
  aryl, such as benzyl, alkoxybenzyl, such as 4-methoxybenzyl, alkoxy, such as methoxymethyl; alkyloxycarbonyloxy; alkyl; alkoxy, such as glycyloxy, phenylglycyloxy, e.g. glycyloxymethyl, phenylglycyloxymethyl; heterocyclyl e.g. 5-methyl-2-oxo-1,3-dioxolen-4-yl;
  indanyl, phthalidyl, alkoxycarbonyloxy and ester moieties which form with the COO— group a physiologically hydrolysable and acceptable ester, e.g. such known to be hydrolysable ester groups in the field of cephalosporins. A compound of formula I may thus be in the form of an physiologically-hydrolysable and -acceptable ester. By physiologically-hydrolysable and -acceptable esters as used herein is meant an ester in which the COO— group is esterified and which is hydrolysable under physiological conditions to yield an acid which is itself physilogically tolerable at dosages to be administered. The term is thus to be understood as defining regular pro-drug forms. An ester moiety may be preferably a group which is easily hydrolysable under physiological conditions. Such esters may be administered preferably orally.

Parenteral administration may be indicated if the ester per se is an active compound or, if hydrolysis occurs in the blood.

In a compound of formula I:

V denotes preferably NO.

$R_1$ denotes preferably hydrogen or alkyl, e.g. lower alkyl, e.g. including unsubstituted alkyl and substituted alkyl; e.g. by halogen, carboxyl, preferably by halogen.

$R_2$ denotes preferably a group of formula a), a'), c), d), d'), e') or f);

$R_4$ denotes preferably hydrogen or alkyl, e.g. lower alkyl.

X and Y independently of each other denote preferably alkylene or alkenylene, e.g. $(C_{1-4})$alkylene or $(C_{1-4})$alkenylene, such as $(C_{2-3})$alkylene or $(C_{2-3})$alkenylene, e.g. including unsubstituted and substituted alkylene or alkenylene, e.g. by
- halogen, alkyl, e.g. lower alkyl; cycloalkyl, carboxyl or alkylcarbonyl; preferably by alkyl, e.g. including hydroxyalkyl, aminoalkyl; carboxyl and (lower alkyl)carbonyl.

$R_5$ denotes preferably hydrogen, alkyl, e.g. including unsubstituted alkyl and substituted alkyl, e.g. by
- hydroxy, carboxyl, amino, e.g. including lower alkylamino or di-lower alkylamino; heterocyclyl, e.g. including 5 or 6 ring members and including one or two heteroatoms, e.g. one, e.g. selected from O, S and N; an ester of a carboxylic-, sulfonic- or phosphoric acid, e.g. an alkyl or aryl ester, e.g. wherein the carboxylic acid part contains 1 to 12 carbon atoms and wherein the ester part contains 1 to 8 carbon atoms; or
- amino-iminomethyl, e.g. of formula

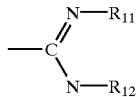

wherein $R_{11}$ and $R_{12}$ independently of each other denote hydrogen or alkyl, e.g. lower alkyl, $R_6$ denotes preferably hydrogen; amino, alkylamino, dialkylamino, e.g. wherein the alkyl part is unsubstituted or substituted, e.g. by hydroxy, amino; arylamino; e.g. $R_6$ denotes a group of formula —$NR_9R_{10}$, wherein $R_9$ and $R_{10}$ independently of each other denote hydrogen, alkyl, e.g. including hydroxyalkyl, aminoalkyl, aryl;

alkyl, e.g. including unsubstituted alkyl and substituted alkyl, e.g. by
- heterocyclyl, e.g. having 5 to 6 ring members and one or two heteroatoms, e.g. selected from N,O,S; e.g. including unsubstituted heterocyclyl and substituted heterocyclyl; e.g. by hydroxy;
- hydroxy; alkoxy, e.g. including unsubstituted alkyoxy and substituted alkoxy, e.g. by hydroxy, alkoxy, amino;
- guanidino, e.g. wherein the amine groups are unsubstituted or substituted, e.g. the terminal amine group is part of heterocyclyl;
- amino, alkylamino, and dialkylamino, e.g. (lower alkyl)amino and (lower dialkyl)amino;
- alkyl, e.g. lower alkyl;
- guanidino; wherein any amine group is unsubstituted or substituted, e.g. by alkyl; hydroxy, cycloalkyl, e.g. including unsubstituted and substituted cycloalkyl, e.g. by amino;

heterocyclyl, e.g. including heterocyclyl having 5 or 6 ring members and one or two heteroatoms, e.g. selected from N,O,S; including e.g. unsubstituted heterocyclyl and substituted heterocyclyl e. g. by alkyl, e.g. $R_6$ denotes a group of formula —$NR_9R_{10'}$, wherein $R_{9'}$ and $R_{10'}$ together with the nitrogen atom to which they are attached form heterocyclyl; or a group of formula —N═$CHR_8$ wherein $R_8$ preferably denotes aryl, heterocyclyl, including substituted and unsubstituted heterocyclyl; e.g. by alkyl; e.g. having 5 or 6 ring members and one or two heteroatoms, e.g. selected from N,O,S;

$R_5$ and $R_6$, if together with the nitrogen atoms to which they are attached form hetercyclyl, denote preferably alkylene, e.g. $(C_{2-4})$alkylene, such as $(C_{2-3})$alkylene;

$R'_6$ denotes preferably alkyl, e.g. lower alkyl;

If $R_6$ and $R_7$ together with the nitrogen atom to which they are attached form hetercyclyl, hetercyclyl having preferably 5 to 7 ring members and one or two hetero atoms, e.g. selected from N,O,S.

In another aspect the present invention provides a compound of formula

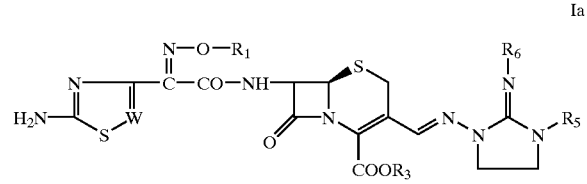

wherein W, $R_1$, $R_3$, $R_5$ and $R_6$ are as defined above.

In another aspect the present invention provides a compound of formula

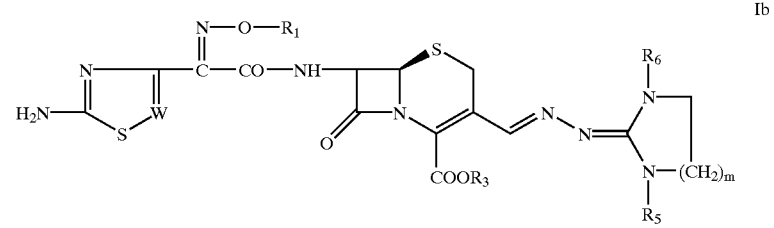

wherein W, $R_1$, $R_3$, $R_5$ and $R_6$ are as defined above and m denotes 1 or 2.

In another aspect the present invention provides the compound 7-{[(5-amino-1,2,4-thiadiazole-3-yl)-(Z)-(fluoromethoxyimino)acetyl]amino}-3-{[(3-ethyl-2-methylimino-imidazolidine-1-yl)imino]methyl}-3-cephem-4-carboxylic acid, e.g. in the form of a hydrochloride.

In this specification unless otherwise indicated terms such as "compound of formula I, Ia and Ib" embrace the compound in any form, for example in the form of a salt and in free base form. The present invention thus includes a compound in free base form or, e.g. where such forms exist, in the form of a salt, for example in the form of an acid addition salt, inner salt, quaternary salt and/or in the form of a solvate, for example in the form of a hydrate. A salt may be a pharmaceutically acceptable salt of a compound of formula I, $I_a$ and $I_b$, such as a metal salt or an amine salt. Metal salts include for example sodium, potassium, calcium, barium, zinc, aluminum salts, preferably sodium or potassium salts. Amine salts include for example trialkylamine, procaine, dibenzylamine and benzylamine salts. A free form of a compound of formula I, Ia and Ib may be converted into a salt form and vice versa.

In a further aspect the present invention provides a compound of formula I, Ia and Ib, in free form and in the form of a salt, for example an acid addition salt or a metal salt; and a compound of formula I, Ia and Ib e.g. in free form or in the form of a salt, in the form of a solvate.

If not otherwise stated herein any carbon containing group may contain up to 20 carbon atoms, e.g. alkyl includes, e.g. straight chain and branched, $(C_{1-20})$, e.g. $(C_{1-8})$alkyl, such as $(C_{1-6})$alkyl and lower alkyl. Lower alkyl includes e.g. $(C_{1-4})$alkyl, such as $(C_{1-2})$alkyl. Cycloalkyl includes, for example $(C_{3-7})$cycloalkyl, particularly $C_3$, $C_5$ or $C_6$ cycloalkyl. Acyl includes alkylcarbonyl and arylcarbonyl, e.g. $(C_{1-12})$acyl, e.g. $(C_{1-6})$acyl, such as $(C_{1-4})$acyl. Aryl includes phenyl, naphthyl, e.g. phenyl. Heterocyclyl includes heterocyclyl having 4 to 7, e.g. 5 to 6 ring members and 1 to 3 nitrogen, sulphur and/or oxygen hetero atoms (N,O,S) including, for example, condensed heterocyclyl, such as for example benzthiazolyl. Amino includes a free amine group, e.g. in the form of a salt, alkylamino, dialkylamino and arylamino, and e.g. protected amino.

Guanidino includes a guanidino group wherein the 3 nitrogen atoms are unsubstituted or independently of each other are substituted, e.g. by alkyl.

If not otherwise stated any group mentioned herein may be unsubstituted or substituted, e.g. one fold or several fold, e.g. by groups which are conventional in β-lactam chemistry, such as by alkyl, e.g. —$CF_3$, aryl, alkoxy, halogen, hydroxy, carboxyl, a sulphonic acid derivative, such as $SO_3H$, a phospshoric acid derivative, acyl, amino; guanidino, heterocyclyl, e.g. pyridyl, oxo, thiono, mercapto, alkyl- or arylthio, imino, alkylimino, CHO.

Halogen includes fluoro, chloro, bromo and iodo.

The present invention includes a compound of formula I in any isomeric from in which it may exist. E.g. the configuration in group —C=V—$R_1$, wherein V—$R_1$ denotes N—O, may be syn [(Z)] and anti [(E)] and is preferably syn [(Z)]. E.g. geometric isomers may be obtained, e.g. during a production process of a compound of formula I, e.g. due to the presence of a —CX'=CX"— double bond wherein X' and X" are groups which have a different meaning. E.g. a chiral carbon atom may be introduced, e.g. during a production process of a compound of formula I and corresponding stereoisomeric forms of a compound of formula I may be obtained, e.g a mixture of the individual stereoisomers, e.g. a racemate, or pure isostercoisomeric forms. Mixtures of isomers may be separated.

The present invention includes a compound of formula I in any tautomeric form. E.g. a compound of formula I, wherein $R_2$ is a group of formula a), wherein $R_5$ is hydrogen, or $R_2$ is a group of formula d), wherein $R_5$ or $R_6$ is hydrogen may exist in a tautomeric form, e.g. as described below:

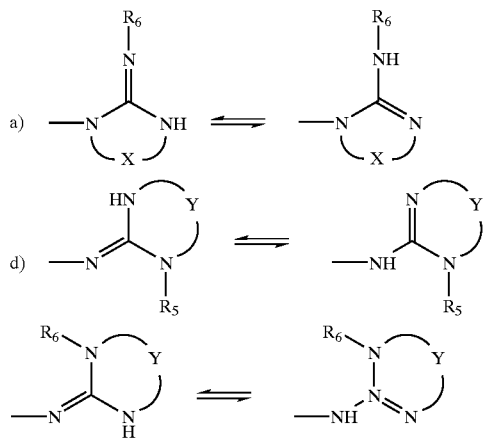

In another aspect the present invention provides a compound of formula

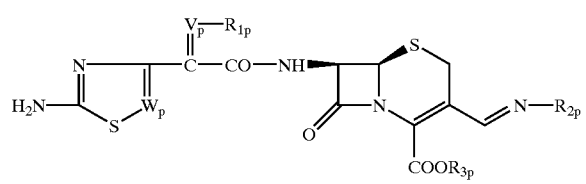

Ip wherein $W_p$ denotes CH or N, $V_p$ denotes =CH— oder =N—O—, $R_{1p}$ denotes hydrogen, acyl, carboxyl, unsubstituted alkyl, or alkyl substituted by halogen or carboxyl, $R_{3p}$ denotes hydrogen, an ester forming group or a cation, $R_{2p}$ denotes a group of formula

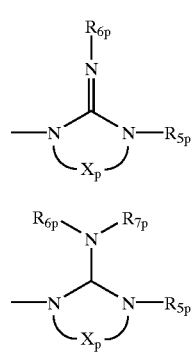

a)

b)

-continued c)
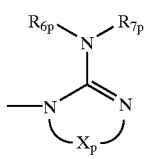

d)
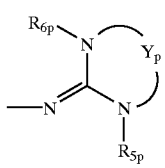

e)
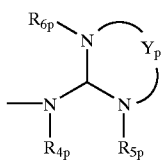

f)
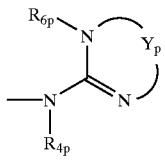

g)
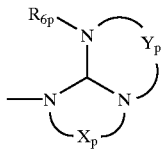

wherein $X_p$ and $Y_p$ are the same or different and each denote a —$(CH_2)_n$-group, wherein n denote a number from 2 to 5, and optionally one or two $CH_2$-groups are replaced by a —CH=CH— group and optionally one or more hydrogen atoms are replaced by halogen, alkyl, cycloalkyl, hydroxyalkyl, aminoalkyl, carboxyl or ethoxycarbonyl, $R_{4p}$ denotes hydrogen, alkyl or hydroxyalkyl, $R_{5p}$ denotes hydrogen, alkyl, (poly)hydroxyalkyl or aminoalkyl, wherein optionally the alkyl groups are additionally substituted by a functional group, e.g. a carboxyl acid residue, a sulphonic acid residue or a phosphoric acid residue, $R_{6p}$ denotes hydrogen, alkyl, hydroxyalkyl, aminoalkyl, amino, hydroxy, alkoxyalkyl, cycloalkyl, a group N=$CHR_{8p}$, wherein $R_{8p}$ denotes aryl or heteroaryl, or a group —$NR_{9p}R_{10}$, wherein $R_{9p}$ und $R_{10p}$ are the same or different and each denote hydrogen, alkyl, hydroxyalkyl or aryl or denote together with the nitrogen atom a saturated, unsubstituted heterocycle with 5 or 6 ring members with one or two nitrogen and/or oxygen atoms, and $R_{7p}$ denotes hydrogen, or $R_{7p}$ and $R_{6p}$ denote together with the nitrogen atom a heterocycle with 5 to 7 ring members containing one or two nitrogen and/or oxygen atoms, with the proviso that, if $W_p$ denotes CH, $V_p$ denotes =N—O—, $R_{1p}$ denotes hydrogen or methyl, $R_{2p}$ denotes a group of formula d) and $R_{3p}$ denotes hydrogen, $R_{5p}$ and $R_{6p}$ denote at the same time another group than hydrogen or methyl, in free form, or, where such forms exist, in the form of acid addition salts, inner salts, quaternary salts or hydrates thereof.

A compound of formula I may be produced e.g. as described below and in the examples, and e.g. analogously to a method as conventional in β-lactam chemistry.

In another aspect the present invention provides a process for the production of a compound of formula I, comprising reacting a compound of formula

II

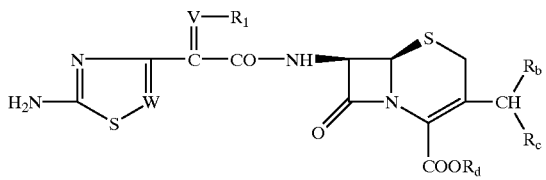

wherein W, V and $R_1$ are as defined above and

α) $R_b$ denotes hydroxy and $R_c$ and $R_d$ together denote a bond, or

β) $R_d$ denotes hydrogen, a cation, an ester forming group or a silyl group, and $R_b$ and $R_c$ together denote the oxo group, in free form or in the form of an acid addition salt thereof with an amine of formula $R_2$—$NH_2$     III wherein $R_2$ is as defined above, e.g. desired (reactive) groups may be protected with protecting groups, e.g. as conventional in β-lactam chemistry, which may be, or, which are split off under the reaction conditions, or after termination of the reaction described above. A compound of formula I wherein $R_3$ denotes hydrogen may be converted into a compound of formula I, wherein $R_3$ denotes an ester moiety, e.g. a carboxylic acid ester group, and vice versa, e.g. by a method analogously to a method as conventional. A compound of formula I may be isolated from the reaction mixture in conventional manner, e.g. analogously to a method as conventional.

E.g. a compound of formula I may be produced as follows:

A compound of formula II may be reacted in a solvent which is inert under the reaction conditions, e.g. a polar solvent, e.g. water and a mixture of water with a lower alcohol or dioxan, or a dipolar aprotic solvent, e.g. dimethylformamide, dimethylsulfoxyde, dimethylacetamide, preferably dimethylacetamide, or a mixture of individual solvents, e.g. as described above, e.g. dimethylacetamide with alcohol or water, e.g. at a temperature from −20 to 50° C. with a compound of formula III. An appropriate, e.g. optimal pH may be adjusted, e.g. by addition of a base or an acid, e.g. an inorganic or an organic acid. A compound of formula I obtained may be isolated from the reaction mixture, e.g. analogously to a method as conventional, e.g. by addition of an anti-solvent to the reaction mixture or, e.g. by chromatography. If desired, any group, e.g. a reactive group, may be protected before reaction, e.g. by silyl protecting group technology in a suitable solvent, e.g. in a solvent which is inert under the reaction conditions, e.g. halogentad carbohydrates, e.g. dichloromethane, nitriles, such as acetonitrile, ethers, e.g.

tetrahydrofurane, or dipolar aprotic solvents, e.g. dimethylformamide, including a mixture of individual solvents, e.g. as defined above. Protecting groups may be split off, e.g. by a deprotection method, e.g. a method as conventional.

Starting compounds are known or may be obtained by a method as conventional, e.g. analogously or e.g. as described in the examples. Starting compounds, e.g. in free form or in the form of a salt, e.g. in the form of a hydrochloride, of formula

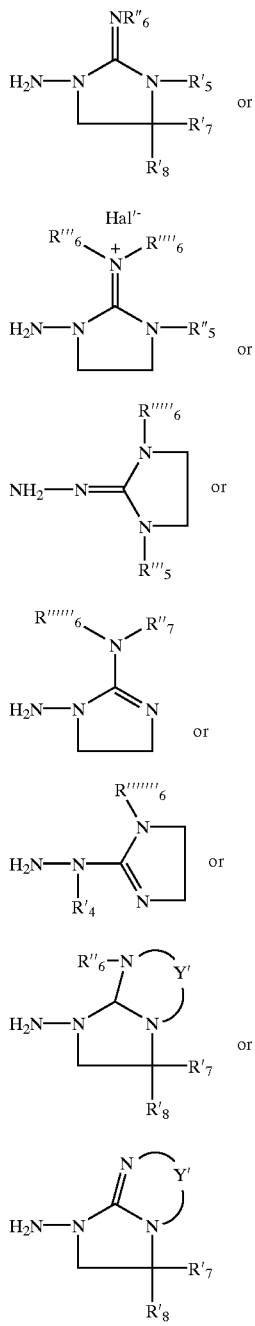

wherein Y' denotes alkylene, e.g. $(C_{2-3})$alkylene,
R'$_5$ denotes hydrogen, alkyl or alkylimino;
  e.g. unsubstituted alkyl, alkyl substituted by hydroxy,
  carboxyl,
  amino, e.g. including an amine group, alkylamino and dialkylamino;
  heterocyclyl, e.g. having 5 or 6 ring members and one or two heteroatoms, selected from N,O,S, e.g. N, e.g. piperidino, pyrrolidino;
  guanidino;
pyridylmethylimino;
R"$_6$ denotes hydrogen, alkyl, hydroxy, alkoxy, cycloalkyl, amino or heterocyclyl;
  e.g. alkylamino, hydroxyalkylamino, phenylamino; unsubsituted alkyl, alkyl substituted by
    heterocyclyl, e.g. having 5 to 6 ring members and containing one or two hetero atoms, e.g. selected from N,O,S, e.g. N, e.g. piperazino, piperidino, pyridino, morpholino, pyridoxal; including unsubstituted heterocyclyl and substituted heterocyclyl, e.g. by alkyl;
    amino, e.g. including an amine group, alkylamino, dialkylamino, hydroxyalkylamino, (di) aminoalkylamino;
    hydroxy, hydroxyalkoxy, alkoxy, e.g. hydroxyalkoxy, alkoxyalkoxy, aminoalkoxyalkoxy;
    guanidino, e.g. wherein the amine groups are unsubstituted or substituted, e.g. by alkyl; e.g. and guanidino wherein the terminal amino group is part of a heterocyclic ring system, e.g. having 5 to 6 ring members and one or two heteroatoms selected from N,O,S; at least from N;
    alkyl, e.g. lower alkyl;
  hetercyclyl, e.g. having 5 to 6 ring members and containing one or two hetero atoms, e.g. selected from N,O,S;
  $(C_{3-7})$cycloalkyl, e.g. unsubstituted cycloalkyl or substituted cycloalkyl by amino;
R'$_7$ and R'$_8$ independently of each other denote hydrogen, carboxyl, alkoxycarbonyl, or alkyl; e.g. lower alkyl, e.g. unsubstituted alkyl and substituted alkyl, e.g. by hydroxy;
R'''$_6$ and R''''$_6$ independently of each other denote alkyl, e.g. lower alkyl; or,
R'''$_6$ and R''''$_6$ together with the nitrogen atom to which they are attached denote heterocyclyl, e.g. having 5 to 6 ring members and containing one or two hetero atoms, e.g. selected from N,O,S; at least one N;
R"$_5$ denotes alkyl, e.g. lower alkyl; or
R"$_5$ and R'''$_6$ together denote alkylene, e.g. $(C_{2-3})$ alkylene;
R'''$_5$ and R''''$_6$ independently of each other denote alkyl, e.g. lower alkyl;
R''''''$_6$ and R"$_7$ together with the nitrogen atom to which they are attached form heterocyclyl, e.g. having 5 or 6 ring members and one or two heteroatoms, e.g. selected from N,O,S, e.g. N;
R'$_4$ and R'''''''$_6$ independently of each other denote alkyl, e.g. lower alkyl; and
Hal denotes halogen, e.g. chloro, bromo;
with the proviso that a compound of formula I$_{Int}$ wherein R'$_5$, R'$_7$ and R'$_8$ are hydrogen and R"$_6$ is hydrogen, 2-(N-morpholino)ethyl, 3-(N,N-dimethylamino) propyl; (2-hydroxyethyl)amino or 2-hydroxyethyl is excluded, are novel.

In another aspect the present invention provides a compound of formula I$_{Int}$, II$_{Int}$, III$_{Int}$, IV$_{Int}$, V$_{Int}$ or VI$_{Int}$, wherein the residues are as defined above, with the proviso as stated above.

The compounds of formula I, hereinafter designated as "active compound(s) of the invention" exhibits pharmacological activity, e.g. beside low toxicity and are therefore useful as pharmaceuticals. In particular, the active compounds of the invention show antimicrobial, e.g. antibacterial, activity against e.g. gram negative and gram positive bacteria, e.g. gram positive bacteria such as Pseudomonas, e.g. *Pseudomonas aeruginosa*; Escherichia, e.g. *Escherichia coli*; Enterobacter, e.g. *Enterobacter cloacae*; Klebsiella, e.g. *Klebsiella edwardsii, Klebsiella pneumoniae*; Enterococcus, e.g. *Enterococcus faecalis*; Moraxella, e.g. *Moraxell catarrhalis*; Streptococcus, e.g. *Streptococcus pneumoniae, Streptococcus pyogenes*; and Staphylococcus, e.g. *Staphylococcus aureus*; in vitro in the Agar Dilution Test according to National Commitee for Clinical Laboratory Standards (NCCLS) 1993, Document M7-A3Vol.13, No. 25: "Methods for dilution Antimicrobial Susceptibility Tests for Bacteria that Grow Aerobically—Third Edition, Approved Standard". The active compounds show an MIC ($\mu$g/ml) in the Agar Dilution Test from about <0.0125 to ca. >25.6. The active compounds of the invention show an surprising overall activity spectrum.

It has, for example, been determined that the MIC ($\mu$g/ml) of the compound of Example 48 against, for example *E. coli* strains ATCC 35218 and ATCC 10536 is of <0.0125; and against *Enterobacter cloacae* strains is of <0.0125.

The active compounds of the invention are, therefore, useful for the treatment of microbial, e.g. bacterial diseases.

In another aspect the present invention provides a compound of claim 1 for use as a pharmaceutical, preferably as an antimicrobial agent, such as an antibiotic. In a further aspect the present invention provides a compound of claim 1 for use in the preparation of a medicament for the treatment of microbial diseases, for example of diseaeses caused by bacterias selected from Pseudomonas, Escherichia, Enterobacter, Kkebsiella, Enterococcus, Moraxella, Streptococcus and Staphylococcus.

In a further aspect the present invention provides a method of treatment of microbial diseases which comprises administering to a subject in need of such treatment an effective amount of a compound of formula I.

For this indication, the appropriate dosage will, of course, vary depending upon, for example, the compound of formula I employed, the host, the mode of administration and the nature and severity of the conditions being treated. However, in general, for satisfactory results in larger mammals, for example humans, an indicated daily dosage is in the range from about 0.05 to 5 g, for example 0.1 to about 2.5 g, of an active compound of the invention conveniently administered, for example, in divided doses up to four times a day.

An active compound of the invention may be administered by any conventional route, for example orally, e.g. in form of tablets or capsules, or parenterally in the form of injectable solutions or suspensions, e.g. in analogous manner to ceftazidime.

The compound 7-{[(5-amino-1,2,4-thiadiazole-3-yl)-(Z)-(fluoromethoxyimino)-acetyl]amino}-3-{[(3-ethyl-2-methylimino-imidazolidine-1-yl)imino]methyl}-3-cephem-4-carboxylic acid, (compound of Example 48) is the preferred compound of the invention for use as an antimicrobial agent.

It has, for example been determined that the MIC ($\mu$g/ml) of the compound of Example 48 (tested in form of the hydrochloride) against, for example *Klebsiella edwardsii*, strain ATCC 10896 is ca. 0.8 whereas, for example ceftazidime shows an MIC ($\mu$g/ml) of ca. 1.6. It is therefore, indicated that for the treatment of microbial diseases, e.g. bacterial diseases the preferred compounds of the invention may be administered to larger mammals, for example humans, by similar modes of administration at similar dosages than conventionally employed with ceftazidime.

The compounds of formula I may be administered in pharmaceutically acceptable salt form, e.g. acid addition salt form or base addition salt form or in the corresponding free forms, optionally in solvate form. Such salts exhibit the same order of activity as the free forms.

The present invention also provides pharmaceutical compositions comprising a compound of formula I in pharmaceutically acceptable salt form or free form in association with at least one pharmaceutical carrier or diluent. Such compositions may be manufactured in conventional manner.

The present invention provides in further aspects a compound of formula I for use as a pharmaceutical in the treatment of microbial diseases caused by bacterias selected from Pseudomonas, Escherichia, Enterobacter, Klebsiella, Moraxella, Enterococcus, Streptococcus, Staphylococcus;

the use of a compound of formula I, or use of a pharmaceutical composition comprising a compound of formula I as a pharmaceutical and a method of treatment of microbial diseases which comprises administering to a subject in need of such treatment an effective amount of a compound of formula I.

In the following examples which illustrate the present invention all temperatures are given in degree Celsius.

The following abbriviations are used:

t-BOC=N-tert.butyloxycarbonyl

BOC anhydride=di-tert.butyldicarbonate

EXAMPLE 1

To a mixture of 0.2 g of 1,2-diamino-4,5-dihydro-1H-imidazole in the form of a dihydrochloride, 0.73 ml of 2 N HCl, 0.57 ml of dimethylacetamide and 0.57 ml of water 0.57 g of N-(1,4,5a,6-tetrahydro-3-hydroxy-1,7-dioxo-3H, 7H-azeto[2,1-b]furo[3,4-d][1,3]-thiazine-6yl)-2-(5-amino-1,2,4-thiadiazole-3-yl)-(Z)-2-fluoromethoxyimino)acetic acid amide are added and the mixture obtained is stirred for ca. 3 hours at room temperature. The mixture obtained is poured onto 150 ml of acetonitrile under stirring. A precipitate is obtained, filtrated off, washed and dried. 7-{[(5-Amino-1,2,4-thiadiazole-3-yl)-(Z)-(fluoromethoxyimino) acetyl]amino}-3-{[(2-amino-4,5-dihydro-1H-imidazole-1-yl)imino]methyl}-3-cephem-4-carboxylic acid in the form of a tri-hydrochloride is obtained in the form of a yellow powder.

For further purification a crude compound obtained is dissolved in water, poured over a chromatography column (LiChroprep RP-18$^R$, Merck) and eluated with water or water/methanol. Fractions containing the desired compound (determined by HPLC) are combined and lyophilized.

Analogously as described in Example 1 the compounds described in TABLE 1 below under Examples (Ex.) 2 to 83, which are compounds of formula I wherein V—$R_1$=N—OCH$_2$F; W is as defined in TABLE 1; $R_3$=hydrogen; and $R_2$ =a compound of formula a), wherein $R_5$ and $R_6$ are as defined in TABLE 1 and X=—CH$_2$CH$_2$—; in the form of a salt as defined in TABLE 1; are obtained:

TABLE 1

| Ex. | W | $R_5$ | $R_6$ | Salt |
|---|---|---|---|---|
| 2 | N | H | —NH—CH$_3$ | 2HCl |
| 3 | N | H | —NH—C$_6$H$_5$ | 2HCl |
| 4 | N | H | CH$_3$ | 2HCl |
| 5 | N | H | —N(piperazine)N—CH$_3$ (4-methylpiperazin-1-yl) | 3HCl |
| 6 | N | H | cyclopropyl | 2HCl |
| 7 | N | H | —CH$_2$CH$_2$—N(piperazine)NH | 3HCl |
| 8 | N | —CH$_2$CH$_2$OH | H | 2HCl |
| 9 | N | H | —CH$_2$CH$_2$—NH—C$_2$H$_5$ | 3HCl |
| 10 | N | H | —CH$_2$CH$_2$—N(CH$_3$)$_2$ | 3HCl |
| 11 | N | H | —CH$_2$CH$_2$—NH$_2$ | HCl |
| 12 | N | H | —NH—CH$_2$CH$_2$OH | HCl |
| 13 | N | H | —(CH$_2$)$_3$—NH$_2$ | HCl |
| 14 | N | H | —CH$_2$CH$_2$—NH—CH$_2$CH$_2$OH | 3HCl |
| 15 | N | —CH$_2$CH$_2$OH | —CH$_2$CH$_2$—N(piperazine)NH | HCl |
| 16 | N | H | —CH$_2$—(4-piperidyl)NH | HCl |
| 17 | N | H | —CH$_2$CH$_2$—(2-pyridyl) | 3HCl |
| 18 | N | H | —CH$_2$CH$_2$—O—CH$_2$CH$_2$OH | HCl |
| 19 | N | H | OH | 2HCl |
| 20 | N | H | —N(morpholine) | 2HCl |
| 21 | N | H | —(CH$_2$)$_4$—NH$_2$ | HCl |
| 22 | N | H | —CH$_2$CH$_2$OH | HCl |
| 23 | N | H | —(CH$_2$)$_6$—NH$_2$ | 3HCl |
| 24 | N | H | —CH$_2$—CH(NH$_2$)CH$_3$ | HCl |
| 25 | N | H | —CH$_2$CH$_2$—N(morpholine) | HCl |
| 26 | N | H | —CH$_2$—C(CH$_3$)$_2$—NH$_2$ | 3HCl |
| 27 | N | H | —C$_2$H$_5$ | 2HCl |
| 28 | N | H | —C$_3$H$_7$ | 2HCl |
| 29 | N | H | —CH$_2$CH$_2$—O—CH$_2$CH$_2$—O—CH$_2$CH$_2$—NH$_2$ | 2HCl |
| 30 | N | H | —(CH$_2$)$_3$—NH—CH$_3$ | 3HCl |
| 31 | N | H | —(CH$_2$)$_3$—NH—CH$_2$CH$_2$OH | HCl |
| 32 | N | H | —(CH$_2$)$_3$—N(CH$_3$)$_2$ | 3HCl |

TABLE 1-continued

| Ex. | W | R$_5$ | R$_6$ | Salt |
|---|---|---|---|---|
| 33 | N | —CH$_2$CH$_2$OH | —(CH$_2$)$_3$—NH$_2$ | HCl |
| 34 | N | —CH$_2$CH$_2$OH | —(CH$_2$)$_3$—NH—CH$_3$ | HCl |
| 35 | N | —CH$_2$CH$_2$OH | —(CH$_2$)$_3$—NH—CH$_2$CH$_2$OH | HCl |
| 36 | N | —CH$_2$CH$_2$OH | —(CH$_2$)$_3$—N(CH$_3$)$_2$ | HCl |
| 37 | N | —CH$_2$CH$_2$OH | —N(CH$_3$)$_2$ | HCl |
| 38 | N | H | —CH$_2$CH$_2$CH$_2$OH | 2HCl |
| 39 | N | —CH$_2$CH$_2$OH | CH$_3$ | 2HCl |
| 40 | N | H | —CH$_2$—CH(OH)—CH$_2$NH$_2$ | 2HCl |
| 41 | N | H | —CH$_2$CH$_2$—N(CH$_2$CH$_2$NH$_2$)$_2$ | 2HCl |
| 42 | N | H | 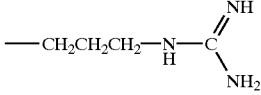 | 3HCl |
| 43 | N | —CH$_2$CH$_2$OH | —C$_2$H$_5$ | 2HCl |
| 44 | N | H | —(CH$_2$)$_3$—NH—(CH$_2$)$_3$—NH$_2$ | 2HCl |
| 45 | N | H | 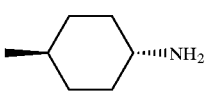 | 3HCl |
| 46 | N | —C$_2$H$_5$ | H | 2HCl |
| 47 | N | H | —CH$_2$—CH(OH)—CH$_2$OH | 2HCl |
| 48 | N | —C$_2$H$_5$ | CH$_3$ | HCl |
| 49 | N | —C$_2$H$_5$ | —(CH$_2$)$_3$—N(CH$_3$)$_2$ | HCl |
| 50 | N | —C$_2$H$_5$ | —(CH$_2$)$_3$—NH$_2$ | HCl |
| 51 | N | —C$_2$H$_5$ | 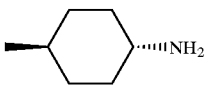 | 3HCl |
| 52 | N | —CH$_2$CH$_2$OH | 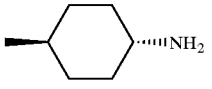 | HCl |
| 53 | N | H | 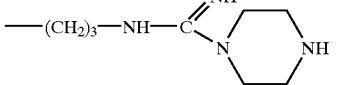 | 4HCl |
| 54 | N | H | 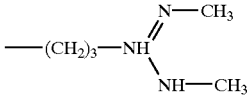 | 2HCl |
| 55 | N | CH$_3$ | H | 2HCl |
| 56 | N | CH$_3$ | CH$_3$ | 2HCl |
| 57 | N | CH$_3$ | —C$_2$H$_5$ | 2HCl |
| 58 | N | CH$_3$ | 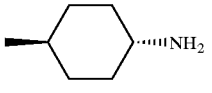 | 3HCl |
| 59 | N | CH$_3$ | —CH$_2$CH$_2$OH | HCl |
| 60 | N | —CH$_2$CH$_2$OH | —CH$_2$CH$_2$OH | HCl |
| 61 | N | —CH$_2$CH$_2$—N(C$_2$H$_5$)$_2$ | H | 2HCl |
| 62 | N | —(CH$_2$)$_3$—N(CH$_3$)$_2$ | H | 2HCl |
| 63 | N | H | —CH$_2$CH$_2$—N(C$_2$H$_5$)$_2$ | 2HCl |
| 64 | N | —CH$_2$CH$_2$—N(C$_2$H$_5$)$_2$ | CH$_3$ | 2HCl |
| 65 | N | —CH$_2$CH$_2$—N(CH$_3$)$_2$ | H | 2HCl |

TABLE 1-continued

| Ex. | W | R₅ | R₆ | Salt |
|---|---|---|---|---|
| 66 | N | H | ![structure: -CH₂- attached to N-hydroxy-pyridinone with ONa substituent] | — |
| 67 | N | H | ![structure: trans-cyclohexane with NH₂, dashed wedge] | HCl |
| 68 | N | H | ![structure: trans-cyclohexane with NH₂, solid wedge] | HCl |
| 69 | N | —CH₂CH₂CH₃ | H | 2HCl |
| 70 | N | —CH₂CH₂CH₃ | CH₃ | 2HCl |
| 71 | N | ![structure: -C(=N-CH(CH₃)₂)-NH-CH(CH₃)₂] | H | 3HCl |
| 72 | N | —CH(CH₃)₂ | H | 2HCl |
| 73 | N | —CH₂CH₂—N(piperidine) | H | 2HCl |
| 74 | N | —(CH₂)₃—CH₃ | CH₃ | 2HCl |
| 75 | N | —(CH₂)₃—CH₃ | H | 2HCl |
| 76 | N | —CH₂CH₂—N(piperidine) | CH₃ | 2HCl |
| 77 | N | —CH₂CH₂—N(pyrrolidine) | H | 2HCl |
| 78 | N | —CH₂COOH | H | 2HCl |
| 79 | N | —(CH₂)₄—CH₃ | H | 2HCl |
| 80 | N | —(CH₂)₅—CH₃ | H | 2HCl |
| 81 | N | —(CH₂)₆—CH₃ | H | 2HCl |
| 82 | N | | —CH₂CH₂— | 2HCl |
| 83 | N | | —CH₂CH₂CH₂— | 2HCl |

EXAMPLE 84

Analogously as described in Example 1, a compound of formula I, wherein V—R₁=N—OCH₂F; R₃=—CH₂—O—CO—C(CH₃)₃; W=N and R₂=a compound of formula a), wherein R₅=—C₂H₅, R₆=CH₃ and X=—CH₂CH₂—; in the form of a hydrochloride is obtained.

Analogously as described in Example 1, the compounds described in TABLE 2 below under Examples (Ex.) 85 to 90 which are compounds of formula I, wherein W=N; V—R₁=N—OCH₂F; R₃=hydrogen; and R₂=a compound of formula a'), wherein R₅, R₆, R₆' and Hal are as defined in TABLE 2 and X=—CH₂CH₂—; in the form of a salt as defined in TABLE 2; are obtained:

TABLE 2

| Ex. | R₅ | R₆ | R'₆ | Hal | Salt |
|---|---|---|---|---|---|
| 85 | —C₂H₅ | CH₃ | CH₃ | Cl | HCl |
| 86 | CH₃ | CH₃ | CH₃ | Cl | HCl |

TABLE 2-continued

| Ex. | $R_5$ | $R_6$ | $R'_6$ | Hal | Salt |
|---|---|---|---|---|---|
| 87 | —$C_2H_5$ | $CH_3$ | —$C_2H_5$ | Cl | HCl |
| 88 | —$CH_2CH_2CH_3$ | $CH_3$ | $CH_3$ | Cl | HCl |
| 89 | —$CH_2CH_2$— | | $CH_3$ | Cl | HCl |
| 90 | —$CH_2CH_2CH_2$— | | $CH_3$ | Cl | HCl |

Analogously as described in Example 1 the compounds described in TABLE 3 below under Examples (Ex.) 91 to 97, which are compounds of formula I wherein W=N; V—$R_1$= N—$OCH_2F$; $R_3$=hydrogen and $R_2$=a compound of formula a), wherein $R_5$, $R_6$ and X are as defined in TABLE 3; in the form of a salt as defined in TABLE 3; are obtained:

TABLE 3

| Ex. | X | $R_5$ | $R_6$ | Salt |
|---|---|---|---|---|
| 91 | —$CH_2$—CH—<br>\|<br>$CH_3$ (wedge) | H | H | 2HCl |
| 92 | —$CH_2$—CH—<br>\|<br>$CH_3$ (wedge) | H | $CH_3$ | 2HCl |
| 93 | —$CH_2$—CH—<br>\|<br>$CH_3$ (wedge up) | H | —$(CH_2)_3$—$NH_2$ | HCl |
| 94 | —$CH_2$—CH—<br>\|<br>$CH_3$ (dashed) | H | —$(CH_2)_3$—$NH_2$ | HCl |
| 95 | $CH_3$<br>\|<br>—$CH_2$—C—<br>\|<br>$CH_3$ | H | H | 2HCl |
| 96 | $CH_3$<br>\|<br>—$CH_2$—C—<br>\|<br>$CH_3$ | H | $CH_3$ | 2HCl |
| 97 | —CH=CH— | $CH_3$ | $CH_3$ | HCl |

Analogously as described in Example 1 the compounds described in TABLE 4 below under Examples (Ex.) 98 to 100 which are compounds of formula I wherein V—$R_1$= N—OH; $R_3$=hydrogen; W is as defined in TABLE 4; and $R_2$=a compound of formula a), wherein $R_5$ and $R_6$ are as defined in TABLE 4 and X=—$CH_2CH_2$—; in the form of a salt as defined in TABLE 4; are obtained:

TABLE 4

| Ex. | W | $R_5$ | $R_6$ | Salt |
|---|---|---|---|---|
| 98 | CH | H | —$(CH_2)_3$—$NH_2$ | HCl |
| 99 | CH | H | —$CH_2CH_2$—$NH_2$ | HCl |
| 100 | CH | —$C_2H_5$ | $CH_3$ | HCl |

Analogously as described in Example 1 the compounds described in TABLE 5 below under Examples (Ex.) 101 to 115 which are compounds of formula I wherein V—$R_1$= N—$OCH_2F$; W=N; $R_3$=hydrogen; and $R_2$=a compound of formula d), wherein $R_5$, $R_6$ and Y are as defined in TABLE 5; in the form of a salt as defined in TABLE 5; are obtained:

TABLE 5

| Ex. | Y | $R_5$ | $R_6$ | Salt |
|---|---|---|---|---|
| 101 | —$CH_2CH_2$— | H | —N=CH—$C_6H_5$ | 2HCl |
| 102 | —$CH_2CH_2$— | H | —$CH_2CH_2OH$ | HCl |
| 103 | —$CH_2CH_2$— | H | H | HCl |
| 104 | —$CH_2CH_2CH_2$— | H | H | 2HCl |
| 105 | —$CH_2CH_2$— | H | —$CH_2CH_2$—$NH_2$ | HCl |
| 106 | —$CH_2CH_2$— | H | —N=CH—(pyridinium)—$CH_3$ | 2HCl |
| 107 | —$CH_2CH_2$— | $CH_3$ | $CH_3$ | 2HCl |
| 108 | —$CH_2CH_2$— | H | —$C_2H_5$ | 2HCl |
| 109 | —$CH_2CH_2$— | H | $CH_3$ | 2HCl |
| 110 | —$CH_2CH_2$— | H | —$CH_2CH_2CH_3$ | 2HCl |
| 111 | —$CH_2CH_2$— | H | —CH($CH_3$)$_2$ | 2HCl |

TABLE 5-continued

| Ex. | Y | R$_5$ | R$_6$ | Salt |
|---|---|---|---|---|
| 112 | —CH$_2$CH$_2$— | —CH(CH$_3$)$_2$ | —CH(CH$_3$)$_2$ | 2HCl |
| 113 | —CH(CH$_3$)—CH— | H | H | 2HCl |
| 114 | —CH(COOCH$_3$)—CH$_2$— | H | H | HCl |
| 115 | —CH(CH$_2$OH)—CH$_2$— | H | H | HCl |

Analogously as described in Example 1 the compounds described in TABLE 6 below under Examples (Ex.) 116 to 118 which are compounds of formula I wherein V—R$_1$ and W are as defined in TABLE 6; R$_3$=hydrogen; and R$_2$=a compound of formula f), wherein R$_4$=CH$_3$, R$_6$ is as defined in TABLE 6 and Y=—CH$_2$CH$_2$—; in the form of a salt as defined in TABLE 6; are obtained:

TABLE 6

| Ex. | W | V-R$_1$ | R$_6$ | Salt |
|---|---|---|---|---|
| 116 | CH | N—OCH$_3$ | CH$_3$ | 2HCl |
| 117 | CH | N—OH | CH$_3$ | 2HCl |
| 118 | N | N—OCH$_2$F | CH$_3$ | 2HCl |

EXAMPLE 119

Analogously as described in Example 1, a compound of formula I, wherein W=N; V—R$_1$=N—OCH$_2$F; R$_3$=hydrogen; and R$_2$=a compound of formula c), wherein R$_6$ and R$_7$ together with the nitrogen atom to which they are attached denote a group of formula

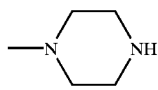

and X=—CH$_2$CH$_2$; in the form of a hydrochloride is obtained.

EXAMPLE 120

Analogously as described in Example 1, a compound of formula I, wherein W=N; V—R$_1$=N—OCH$_2$F; R$_3$=hydrogen; and R$_2$=a compound of formula d'), wherein R$_5$ and R$_6$=hydrogen; in the form of a dihydrochloride is obtained.

Substituted 1,2-diamino-4,5-dihydro-1H-imidazoles are obtained as follows:

EXAMPLE A a. 5 g of 1-benzylideneamino-imidazolidine-2-thion are suspended in 40 ml of methanol and treated with 1.7 ml of methyliodide. The mixture obtained is refluxed for ca. one hour and the solvent is evaporated off. 1-Benzylideneamino-2-methylthio-4,5-dihydro-1H-imidazole in the form of a hydroiodide is obtained in solid form, to which 120 ml of water and 70 ml of an anion exchange resin in chloride form (Amberlite IRA-400 (Cl)$_R$) are added. The mixture is stirred for ca. 2 hours at room temperature, filtrated and lyophilized. 1-Benzylideneamino-2-methylthio-4,5-dihydro-1H-imidazole in the form of a hydrochloride is obtained in the form of a lyophilisate.

b. 1 g of 1-benzylideneamino-2-methylthio-2-imidazoline in the form of a hydrochloride in 10 ml of methanol are treated with 0.33 ml of NH$_3$ (28% in H$_2$O). The mixture obtained is refluxed for ca. 5 hours and a precipitate obtained is filtrated off. From the filtrate obtained the solvent is evaporated off. The residue obtained is treated with acetonitrile. The precipitate obtained is filtrated off and dried. Solid 2-amino-1-benzylideneamino-4,5-dihydro-1H-imidazole in the form of a hydrochloride is obtained.

c. From a mixture of 0.89 g of derivative of 2-amino-1-benzylideneamino-4,5-dihydro-1H-imidazole in the form of a hydrochloride in 5.9 ml of 2 N HCl, benzaldehyde is distilled off by steam distillation. The solvent from the remaining mixture is evaporated off. Solid 1,2-diamino-4,5-dihydro-1H-imidazole in the form of a dihydrochloride is obtained.

EXAMPLE B

A mixture of 0.79 g of 1-benzylideneamino-2-methylthio-4,5-dihydro-1H-imidazole in the form of a hydrochloride in 10 ml of methanol with 0.18 ml of hydrazine hydrate is stirred for ca. 6 hours at room temperature. From the mixture obtained the solvent is evaporated off and the residue is treated with acetonitrile. 1-benzylidene-amino-2-hydrazino-4,5-dihydro-1H-imidazole precipitates, is filtrated off and dried.

EXAMPLE C a. 0.58 g of 1-(β-aminoethyl)imidazolidine-2-thion in 25 ml of dichloromethane are treated with 0.96 g of BOC-anhydride. The mixture obtained is stirred for ca. 4 hours at room temperature and the solvent is evaporated off. Solid 1-[β-(t-BOC-aminoethyl)]imidazolidine-2-thion is obtained.

b. A mixture of 0.5 g of β-(t-BOC-aminoethyl)]imidazolidine2-thion in 20 ml of methanol and 0.32 g of methyliodide are refluxed for ca. one hour and the solvent is evaporated off. 1-[β-(t-BOC-aminoethyl)]-2-methylthio-4,5-dihydro-1H-imidazole in the form of a hydroiodide is obtained and is stirred in 20 ml of water and an anion exchange resin in chloride form (6 ml of IRA-400(Cl)$^R$) for ca. one hour at room temperature. From the mixture obtained the anion exchange resin is filtrated off and the filtrate obtained is lyophilized. 1-[β-(t-BOC-aminoethyl)]-2-methylthio-4,5-dihydro-1H-imidazole is obtained in the form of a lyophilisate.

c. A mixture of 1.06 g of 1-[β-(t-BOC-aminoethyl)]-2-methylthio-4,5-dihydro-1H-imidazoline in 25 ml of methanol and 0.2 g of hydrazine hydrate are refluxed for ca. 2 hours and the solvent is evaporated off. Solid 1-[β-(t-BOC-aminoethyl)]-2-hydrazino-4,5-dihydro-1H-imidazole is obtained.

EXAMPLE D a. The pH of a solution of 1.59 g of 1-benzylideneamino-4,5-dihydro-2-methylamino-1H-imidazole in the form of a hydrochloride in 40 ml of water is adjusted to 12.0 with 2 M NaOH. The mixture obtained is extracted with dichloromethane. The organic phase is dried over Na$_2$SO$_4$ and evaporated off. 1-benzylideneamino-4,5-dihydro-2-methylamino-1H-imidazole is obtained in the form of a powder.

b. A mixture of 1 g of 1-benzylideneamino-4,5-dihydro-2-methylamino-1H-imidazole in 30 ml of acetonitrile with 1.26 g of propyliodide is refluxed for ca. 8 hours. The mixture obtained is stirred overnight at room temperature. 1-Benzylideneamino-2-methylimino-3-propyl-imidazolidine in the form of a hydroiodide precipitates, is filtrated off and dried.

c. A mixture of 0.70 g of 1-benzylideneamino-2-methylimino-3-propyl-imidazolidine in the form of a hydroiodide in 20 ml of water H$_2$O with 10 ml of an anion exchange resin in chloride form (Amberlite IRA-400 (Cl)$^R$) is stirred for ca. 3 hours at room temperature, the anion exchange resin is filtrated off and the filtrate obtained is treated with 3.6 ml of 2 M HCl. Benzaldehyde is distilled off from the mixture obtained by steam distillation. From the remaining mixture the solvent is evaporated off. 1-Amino-2-methylimino-3-propyl-imidazolidine in the form of a hydrochloride is obtained in the form of an oil.

EXAMPLE E a. A mixture of 0.89 g of 1-benzylideneamino-2-methylimino-3-propyl-imidazolidine in the form of a hydroiodide in 20 ml H$_2$O with 10 ml of an anion exchange resin in chloride form (Amberlite IRA-400 (Cl)$^R$) is stirred for ca. 3 hours at room temperature, the anion exchange resin is filtrated off and the pH of the filtrate obtained is adjusted to 12.6 with 2 M NaOH. 1-Benzylideneamino-2-methylimino-3-propyl-imidazolidine precipitates, is filtrated off, dried and obtained in the form of a powder.

b. A mixture of 0.51 g of 1-benzylideneamino-2-methylimino-3-propyl-imidazolidine in 15 ml of acetonitrile with 0.36 g of methyliodide is refluxed for ca. one hour and the solvent is evaporated off. The residue is treated with acetonitrile and the solvent is evaporated off. (1-benzylideneamino-3-propyl-imdazolidine-2-yliden)methyl-ammonium iodide is obtained in the form of a powder.

c. Solid (1-amino-3-propyl-imidazolidine-2-yliden)-dimethyl-ammoniumchloride in the form of a hydrochloride is obtained analogously as described in Example D, c.

EXAMPLE F

A mixture of 0.72 g of 2-(3-amino-propylimino)-imidazolidine-1-yl-benzylideneamine in 15 ml of absolute ethanol with 0.53 g of S-methylisothiourea chloride is refluxed for ca. 4 hours and the solvent is evaporated off. The residue obtained, dissolved in 4 ml of 2 M HCl and 4 ml of H$_2$O, is poured over a chromatography column (LiChroprep RP-18$^R$, Merck) and eluated with water. Fractions obtained containing 2-(3-guanidino-propylimino)-imidazolidine-1-yl-benzylideneamine in the form of a hydrochloride (determination by HPLC) are combined. Benzaldehyde is distilled off from a mixture of the combined fractions obtained with 2 M HCl by steam distillation. From the remaining mixture the solvent is evaporated off. Solid 2-(3-guanidino-propylimino)-imdazolidine-1-yl-amine in the form of a dihydrochloride is obtained.

EXAMPLE G a. A mixture of 1.61 g of 2-(3-amino-propylimino)-imidazolidine-1-yl-benzylidene-amine in 25 ml of dichloromethane with 0.48 g of methylisothiocyanate is stirred for ca. 90 minutes at room temperature and the solvent is evaporated off. The residue obtained is treated with 40 ml of H$_2$O and the pH of the mixture obtained is adjusted to 1.00 with 2 M HCl. 1-[2-(1-Benzylideneamino-imidazolidine-2-ylidene-amino)-propyl]-3-methyl-thiourea in the form of a hydrochloride precipitates, is filtrated off, dried and obtained in the form of a powder.

b. A mixture of 1.79 g of 1-[2-(1-benzylideneamino-imidazolidine-2-ylidene-amino)-propyl]-3-methyl-thiourea in the form of a hydrochloride in 30 ml of methanol with 0.52 ml of methyliodide are refluxed for ca. 3 hours, the solvent is evaporated off and the residue obtained is stirred with 80 ml of H$_2$O and 30 ml of an anion exchange resin in chloride form (Amberlite IRA-400 (Cl)$^R$) for ca. 2 hours. From the mixture obtained the ion exchange resin is filtrated off and the filtrate obtained is lyophilized. 1-[(1-Benzylideneamino-imidazolidine-2-ylidene-amino)-propyl]-3-methyl-2-methyl-isothiourea in the form of a hydrochloride is obtained in the form of a lyophilisate.

c. A mixture of 1 g of 1-[(1-benzylideneamino-imidazolidine-2-ylidene-amino)-propyl]-3-methyl-2-methyl-isothiourea in the form of a hydrochloride with 0.54 ml of methylamine (33% solution in absolute ethanol) and 30 ml of methanol is refluxed for ca. 7 hours and the solvent is evaporated off. The residue obtained, dissolved in 4 ml of 2 M HCl and 6 ml of H$_2$O, is poured over a chromatography column (LiChroprep RP-18$^R$, Merck) and eluated with H$_2$O/methanol. The fractions containing 2-[3-(N,N'-dimethylguanidino)-propylamino]-imidazolidine-1-yl-benzylideneamine in the form of a hydrochloride (determination by HPLC) are combined and the combined fractions obtained are lyophilized.

d. Benzylaldehyde is distilled off from a solution of 0.5 g of the derivative of 2-[3-(N,N'-dimethylguanidino)-propylamino]-imidazolidine-1-yl-benzylideneamine in the form of a hydrochloride in 2.1 ml of 2 M HCl by steam distillation. 2-[3-(N,N-dimethyl-guanidino)-propylamino]-imidazolidine-1-yl-amine in the form of a dihydrochloride is obtained by solvent evaporation from the remaining residue.

EXAMPLE H a. 0.99 ml of N,N'-diisopropylcarbodiimid in 10 ml of dichloromethane are added dropwise to a solution 1 g of 2-amino-1-benzylideneamino-4,5-dihydro-1H-imidazole in 20 ml of dichloromethane within ca. 30 minutes, the mixture obtained is stirred for ca. 6 days at room temperature and the solvent is evaporated off. The residue obtained is dissolved in 6 ml of 2 M HCl and 4 ml of $H_2O$, poured over a chromatography column (LiChroprep RP-18$^R$, Merck) and eluated with water. Fractions containing 1-benzylideneamino-3-(N,N'-diisopropyl-guanidino)-2-imino-imidazolidine (HPLC determination) are combined and lyophilized.

b. Solid 1-amino-3-(N,N'-diisopropylguanidino)-2-imino-imidazolidine in the form of a dihydrochloride is obtained by removing benzylaldehyde from 1-benzylideneamino-3-(N,N'-diisopropylguanidino)-2-imino-imidazolidine analogously as described in Example G, d.

EXAMPLE I a. A mixture of 3 g of 2-[(1-benzylideneamino-4,5-dihydro-1H-imidazole-2-yl)amino]ethanol in 50 ml of methylene chloride with 1.22 ml of thionyl chloride is stirred for ca. 1 hour at room temperature. 2-(2-chloro-ethylimino)-imidazolidine-1-yl-benzylideneamine precipitates, is filtrated off and dried.

b. A mixture of 3.7 g of 2-(2-chloro-ethylimino)-imidazolidine-1-yl-benzylideneamine in 50 ml of absolute ethanol with 2.25 ml of N-ethyldiisopropylamine is refluxed for ca. 22 hours, the solvent is evaporated off and the residue obtained is treated with acetonitrile. Solid 2,3,5,6-tetrahydro-imidazo[1,2a]imidazole-1-yl-benzylideneamine in the form of a hydrochloride is obtained.

c. Solid 2,3,5,6-tetrahydro-imidazole[1,2a]imidazole-1-ylamine in the form of a hydrochloride is obtained by removing benzylaldehyde from 2,3,5,6-tetrahydro-imidazo[1,2a]imidazole-1-yl-benzylideneamine in the form of a hydrochloride analogously as described in Example G, d.

EXAMPLE J a. A mixture of 4 g of hydrazino-acetaldehyd diethylacetal in 40 ml of ethanol is stirred with 1.97 g of methylisothiocyanate for ca. 4 hours at room temperature, the solvent is evaporated off and 2-(2,2-diethoxy-ethyl)-4-methyl-thiosemicarbazide is obtained in crystalline form.

b. A mixture of 4 g of 2-(2,2-diethoxy-ethyl)-4-methyl-thiosemicarbazide and 2.82 g of methyliodide in 40 ml of methanol is refluxed for ca. 90 minutes and the solvent is evaporated off. 4.53 g of 2-(2,2-diethoxy-ethyl)-3,4-dimethyl-isothiosemicarbazide in the form of a hydroiodide are obtained which are dissolved in water and stirred with a strong basic ion exchange resin in chloride form (Amberlite IRA 400 (Cl)$^R$) for ca. 2.5 hours. The ion exchange resin is filtrated off and the filtrate obtained is lyophilized. 2-(2,2-Diethoxy-ethyl)-3,4-dimethyl-isothiosemicarbazide in the form of a hydrochloride is obtained in the form of an oil.

c. A mixture of 2 g of 2-(2,2-diethoxy-ethyl)-3,4-dimethyl-isothiosemicarbazide in the form of a hydrochloride in 20 ml of ethanol with 0.91 ml of methylamine (33% solution in absolute ethanol) is stirred for ca. 26 hours at room temperature. To the mixture obtained 0.91 g of benzylaldehyde are added. The mixture obtained is stirred for ca. 21 hours, the solvent is evaporated off and the residue is treated with diethylether. 1-(Benzylideneamino)-1-(2,2-diethoxy-ethyl)-2,3-dimethyl-guanidine in the form of a hydrochloride in resin-like form is obtained.

d. A mixture of 1.39 g of 1-(benzylideneamino)-1-(2,2-diethoxy-ethyl)-2,3-dimethyl-guanidine in the form of a hydrochloride with 5 ml of hydrochloric acid conc. is stirred for ca. 30 minutes at room temperature. The pH of the mixture obtained is adjusted to 6.4 with 1 N NaOH. The mixture obtained is extracted with diethylether. The pH of the aqueous phase is adjusted to 12 with 1 N NaOH. The mixture obtained is extracted with dichloromethane. The organic phase is dried over $Na_2SO_4$, the solvent is evaporated off and benzylidene-(3-methyl-2-methylimino-2,3-dihydro-imidazolel-1-yl)-amine is obtained in the form of an oil.

c. Benzylaldehyde is removed from 384 mg of benzylidene-(3-methyl-2-methylimino-2,3-dihydro-imidazolel-1-yl)-amine in 10 ml of water and 3.55 ml of 2 N HCl analogously as described in Example G, d. and 3-methyl-2-methylimino-2,3-dihydro-imidazole-1-ylamine in the form of a dihydrochloride is obtained in the form of an oil.

EXAMPLE K a. 0.6 ml of $CS_2$ are added dropwise to a solution of 1.7 g of potassium hydroxide in 6 ml of water and 14 ml of ethanol under stirring. The mixture obtained is refluxed for ca. 4 hours with 1.47 g of (R,S)-2,3-diamino-1-propanol in the form of a dihydrochloride. The pH of the mixture obtained is adjusted to 2 with 6 N hydrochloric acid and the solvent is evaporated off. The residue obtained is treated with ethanol and with methanol. KCl precipitates and is filtrated off. The solvent from the filtrate obtained is evaporated off and solid (R,S)-4-hydroxymethyl-imidazolidine-2-thion is obtained.

b. A mixture of 1.4 g of (R,S)-4-hydroxymethyl-imidazolidine-2-thion in 25 ml of methanol with 1.8 g of methyliodide is refluxed for ca. 2 hours, the solvent is evaporatd off and 2.26 g of (R,S)-2-methylthio-4,5-dihydro-1H-imidazole-4-yl)-methanol in the form of a hydroiodide are obtained, are dissolved in 4 ml of water and poured over a column filled with a strong basic ion exchange resin in chloride form (Amberlite IRA 400$^R$) and are eluated with water. The fractions containing (R,S)-2-methylthio-4,5-dihydro-1H-imidazole-4-yl)-methanol in the form of a hydrochloride (HPLC determination) are combined and lyophilized.

c. A mixture of 1.54 g of (R,S)-2-methylthio-4,5-dihydro-1H-imidazole-4-yl)-methanol in the form of a hydrochloride dissolved in methanol with 462 mg of hydrazine hydrate is stirred for ca. one day at room temperature, the solvent is evaporated off and the residue obtained is dissolved in ethanol and treated with etheric hydrochloric acid. (R,S)-2-Hydrazono-imidazolidine-4-yl)-methanol in the form of a dihydrochloride in crystalline form is obtained.

EXAMPLE L a. 2.86 ml of $CS_2$ are added dropwise to a solution of 7.9 g of potassium hydroxide in 30 ml of water and 64 ml of ethanol under stirring. The mixture obtained is refluxed for ca. 4 hours with 6.0 g of DL-2,3-diamino-propionic acid in the form of a hydrochloride. The pH of the mixture obtained is adjusted to 2 with 6 N hydrochloric acid and the solvent is evaporated off. Solid (R,S)-2-thioxo-imidazolidine-4-carboxylic acid is obtained and is stirred overnight with 150 ml of methanol under addition of 5 ml of 1 N etheric hydrochloric acid. KCl precipitates and is filtrated off. The solvent from the filtrate obtained is evaporated off and solid (R,S)-2-thioxo-imidazolidine-4-carboxylic acid methylester is obtained.

b. A mixture of 6 g of (R,S)-2-thioxo-imidazolidine-4-carboxylic acid methylester in 100 ml of methanol with 4 g of methyliodide is refluxed for ca. 2 hours, the solvent is evaporated off and 5 g of (R,S)-2-methylthio-4,5-dihydro-1H-imidazole-4-carboxylic acid methylester in the form of a hydroiodide are obtained in solid form, which is dissolved in 30 ml of water. To the solution obtained 3 g of sodium carbonate are added in portions. The aquous solution obtained is extracted with dichloromethane, the organic phase is dried over $Na_2SO_4$ and the solvent is evaporated off. Solid (RS)-2-methylthio-4,5-dihydro-1H-imidazole-4-carboxylic acid methylester is obtained.

c. A mixture of 1.36 g of (R,S)-2-methylthio-1H-imidazole-4-carboxylic acid methylester in 15 ml of methanol with 710 mg of hydrazine in the form of a monohydrochloride and 1 ml of water is stirred overnight at room temperature and the solvent is evaporated off. Solid (R,S)-2-hydrazono-imidazolidine-4-carboxylic acid methylester in the form of a hydrochloride is obtained.

Analogously as described in Example A to Example L the compounds described in Example M to Example CZ below are obtained:

EXAMPLE M TO EXAMPLE CK

Compounds of formula

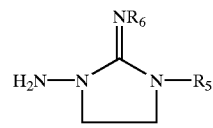

a)

wherein $R_5$ and $R_6$ are as defined in TABLE 7 below in the form of a salt as defined in TABLE 7 below (Ex.=Example):

TABLE 7

| Ex. | $R_5$ | $R_6$ | Salt |
|---|---|---|---|
| M | H | —NH—$CH_3$ | HCl |
| N | H | —NH—$C_6H_5$ | 2HCl |
| O | H | $CH_3$ | 2HCl |
| P | H | —$CH_2CH_2$—N⟨piperazine⟩NH | 2HCl |
| Q | —$CH_2CH_2OH$ | H | 2HCl |
| R | H | —$CH_2CH_2$—NH—$C_2H_5$ | 2HCl |
| S | H | —$CH_2CH_2$—$N(CH_3)_2$ | 2HCl |
| T | H | —$CH_2CH_2$—$NH_2$ | 2HCl |
| U | H | —NH—$CH_2CH_2OH$ | 2HCl |
| V | H | —$(CH_2)_3$—$NH_2$ | 2HCl |
| W | H | —$CH_2CH_2$—NH—$CH_2CH_2OH$ | 2HCl |
| X | —$CH_2CH_2OH$ | —$CH_2CH_2$—N⟨piperazine⟩NH | 2HCl |
| Y | H | —$CH_2$—⟨piperidine⟩NH | 2HCl |
| Z | H | —$CH_2CH_2$—⟨pyridine⟩ | 2HCl |
| AA | H | —$CH_2CH_2$—O—$CH_2CH_2OH$ | 2HCl |
| AB | H | OH | 2HCl |
| AC | H | —N⟨morpholine⟩O | 2HCl |
| AD | H | —$(CH_2)_4$—$NH_2$ | 2HCl |
| AE | H | —$CH_2CH_2OH$ | 2HCl |
| AF | H | —$(CH_2)_6$—$NH_2$ | 2HCl |
| AG | H | —$CH_2CH$(NH_2)(CH_3)$ | 2HCl |
| AH | H | —$CH_2CH_2$—N⟨morpholine⟩O | 2HCl |

TABLE 7-continued

| Ex. | R$_5$ | R$_6$ | Salt |
|---|---|---|---|
| AI | H | —CH$_2$—C(CH$_3$)$_2$—NH$_2$ | 2HCl |
| AJ | —N=CH—(1-methylpyridinium-4-yl) Cl$^-$ | —NH$_2$ | 2HCl |
| AK | H | —N(4-methylpiperazin-1-yl) | 2HCl |
| AL | H | —cyclopropyl | 2HCl |
| AM | H | —C$_2$H$_5$ | 2HCl |
| AN | H | —C$_3$H$_7$ | 2HCl |
| AO | H | —CH$_2$CH$_2$—O—CH$_2$CH$_2$—O—CH$_2$CH$_2$—NH$_2$ | 2HCl |
| AP | H | —(CH$_2$)$_3$—NH—CH$_3$ | 2HCl |
| AQ | H | —(CH$_2$)$_3$—NH—CH$_2$CH$_2$OH | 2HCl |
| AR | H | —(CH$_2$)$_3$—N(CH$_3$)$_2$ | 2HCl |
| AS | —CH$_2$CH$_2$OH | —(CH$_2$)$_3$—NH$_2$ | 2HCl |
| AT | —CH$_2$CH$_2$OH | —(CH$_2$)$_3$—NH—CH$_3$ | 2HCl |
| AU | —CH$_2$CH$_2$OH | —(CH$_2$)$_3$—NH—CH$_2$CH$_2$OH | 2HCl |
| AV | —CH$_2$CH$_2$OH | —(CH$_2$)$_3$—N(CH$_3$)$_2$ | 2HCl |
| AW | —CH$_2$CH$_2$OH | —N(CH$_3$)$_2$ | 2HCl |
| AX | H | —(CH$_2$)$_3$—OH | 2HCl |
| AY | —CH$_2$CH$_2$OH | CH$_3$ | 2HCl |
| AZ | H | —CH$_2$—CH(OH)—CH$_2$—NH$_2$ | 2HCl |
| BA | H | —CH$_2$CH$_2$—N(CH$_2$CH$_2$NH$_2$)$_2$ | 2HCl |
| BB | —CH$_2$CH$_2$OH | —C$_2$H$_5$ | 2HCl |
| BC | H | —CH$_2$CH$_2$—NH—(CH$_2$)$_3$—NH$_2$ | 3HCl |
| BD | H | trans-4-aminocyclohexyl | 3HCl |
| BE | —C$_2$H$_5$ | H | 2HCl |
| BF | H | —CH$_2$—CH(OH)—CH$_2$OH | 2HCl |
| BG | —C$_2$H$_5$ | CH$_3$ | 2HCl |
| BH | —C$_2$H$_5$ | —(CH$_2$)$_3$—N(CH$_3$)$_2$ | 2HCl |
| BI | —C$_2$H$_5$ | —(CH$_2$)$_3$—NH$_2$ | 3HCl |
| BJ | —C$_2$H$_5$ | trans-4-aminocyclohexyl | 3HCl |
| BK | —CH$_2$CH$_2$OH | trans-4-aminocyclohexyl | 3HCl |
| BL | H | —(CH$_2$)$_3$—NH—C(=NH)—(piperazin-1-yl) | 3HCl |
| BM | CH$_3$ | H | 2HCl |
| BN | CH$_3$ | CH$_3$ | 2HCl |
| BO | CH$_3$ | —C$_2$H$_5$ | 2HCl |
| BP | CH$_3$ | trans-4-aminocyclohexyl | 3HCl |
| BQ | CH$_3$ | —CH$_2$CH$_2$OH | 2HCl |
| BR | —CH$_2$CH$_2$OH | —CH$_2$CH$_2$OH | 2HCl |

TABLE 7-continued

| Ex. | R₅ | R₆ | Salt |
|---|---|---|---|
| BS | —CH₂CH₂—N(C₂H₅)₂ | H | 2HCl |
| BT | —(CH₂)₃—N(CH₃)₂ | H | 2HCl |
| BU | H | —CH₂CH₂—N(C₂H₅)₂ | 2HCl |
| BV | —CH₂CH₂—N(C₂H₅)₂ | CH₃ | 2HCl |
| BW | —CH₂CH₂—N(CH₃)₂ | H | 2HCl |
| BX | H | ![pyridinone structure: —CH₂— attached to a pyridine ring with =O, —OH, and N—OH substituents] | HCl |
| BY | H | ![cyclohexane with CH₃ and NH₂ substituents] | 3HCl |
| BZ | —CH₂CH₂CH₃ | H | 2HCl |
| CA | —CH(CH₃)₂ | H | 2HCl |
| CB | —CH₂CH₂—N(piperidine) | H | 2HCl |
| CC | —(CH₂)₃—CH₃ | CH₃ | 2HCl |
| CD | —(CH₂)₃—CH₃ | H | 2HCl |
| CE | —CH₂CH₂—N(piperidine) | CH₃ | 2HCl |
| CF | —CH₂CH₂—N(pyrrolidine) | H | 2HCl |
| CG | —CH₂—COOH | H | 2HCl |
| CH | —(CH₂)₄—CH₃ | H | 2HCl |
| CI | —(CH₂)₅—CH₃ | H | 2HCl |
| CJ | —(CH₂)₆—CH₃ | H | 2HCl |
| CK |  | —CH₂CH₂CH₂— | 2HCl |

EXAMPLE CL TO EXAMPLE CP

Compounds of formula

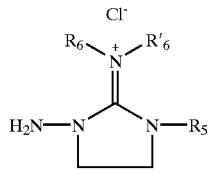

a')

wherein $R_5$, $R_6$ and $R'_6$ are as defined in TABLE 8 below in the form of a salt as defined in TABLE 8 below (Ex.= Example):

TABLE 8

| Ex. | R₅ | R₆ | R'₆ | Salt |
|---|---|---|---|---|
| CL | —C₂H₅ | CH₃ | CH₃ | HCl |
| CM | CH₃ | CH₃ | CH₃ | HCl |
| CN | —C₂H₅ | —C₂H₅ | CH₃ | HCl |
| CO | —CH₂CH₂— | | CH₃ | HCl |
| CP | —CH₂CH₂CH₂— | | CH₃ | HCl |

EXAMPLE CQ TO EXAMPLE CU

Compounds of formula

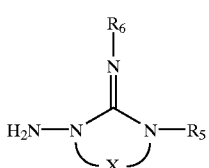

a)

wherein $R_5$, $R_6$ and X are as defined in TABLE 9 below in the form of a salt as defined in TABLE 9 below (Ex.= Example):

TABLE 9

| Ex. | $R_5$ | $R_6$ | X | Salt |
|---|---|---|---|---|
| CQ | H | $CH_3$ | $-CH_2-\underset{CH_3}{CH}-$ | 2HCl |
| CR | H | H | $-CH_2-\underset{CH_3}{CH}-$ | 2HCl |
| CS | H | $-(CH_2)_3-NH_2$ | $-CH_2-\underset{CH_3}{CH}-$ | 3HCl |
| CT | H | $CH_3$ | $-CH_2-\underset{\underset{CH_3}{\mid}}{\overset{\overset{CH_3}{\mid}}{C}}-$ | 2HCl |
| CU | H | H | $-CH_2-\underset{\underset{CH_3}{\mid}}{\overset{\overset{CH_3}{\mid}}{C}}-$ | 2HCl |

EXAMPLE CV to Example CX

Compounds of formula

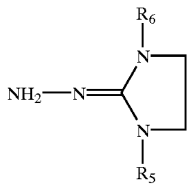

(d)

wherein $R_5$ and $R_6$ are as defined in TABLE 10 below in the form of a salt as defined in TABLE 10 below (Ex.= Example):

TABLE 10

| Ex. | $R_5$ | $R_6$ | Salt |
|---|---|---|---|
| CV | $-CH_2CH_2CH_3$ | H | HCl |
| CW | $-CH(CH_3)_2$ | H | HCl |
| CX | $-CH(CH_3)_2$ | $-CH(CH_3)_2$ | HCl |

EXAMPLE CY

A compound of formula

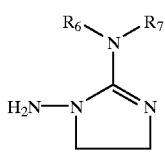

(c)

wherein $R_6$ and $R_7$ together with the nitrogen atom to which they are attached denote a group of formula

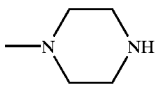

in the form of a dihydrochloride.

EXAMPLE CZ

A compound of formula

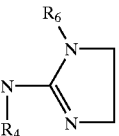

(f)

wherein $R_4=CH_3$ and $R_6=CH_3$ in the form of a hydrochloride.

EXAMPLE DA

A cooled mixture of 68.5 ml (ca. −5°) of 2 N $H_2SO_4$ with 4 g 1-(2-hydroxyethyl)-3-nitrosoimidazolidine-2-thion is treated with 3.42 g of Zn-powder, the mixture obtained is stirred for ca. 15 minutes and filtrated. The filtrate obtained is treated with 2.88 ml of benzylaldehyde and stirred for ca. one hour at room temperature. 1-Benzylideneamino-3-(2-hydroxyethyl)imidazolidine-2-thion precipitates, is filtrated off, washed with diethylether and dried.

Analogously as described in Example DA 1-benzylideneamino-3-ethyl-imidazolidine-2-thion is obtained from 1-ethyl-3-nitrosoimidazolidine-2-thion, 1-benzylideneamino-3-methyl-imidazolidine-2-thion is obtained from 1-methyl-3-nitrosoimidazolidine-2-thion, 1-benzylideneamino-3-propyl-imidazolidine-2-thion is obtained from 1-propyl-3-nitrosoimidazolidine-2-thion, 1-benzylideneamino-4-methyl-imidazolidine-2-thion is obtained from 1-nitroso-4-methyl-imidazolidine-2-thion, and 1-benzylideneamino-4,4-dimethyl-imidazolidine-2-thion is obtained from 4,4-dimethyl-3-nitroso-imidazolidine-2-thion.

EXAMPLE DB

To an ice-cooled mixture of 6.81 g of 1-ethyl-imidazolidine-2-thion and 3.6 g of $NaNO_2$ in 440 ml of dichloromethane 63 ml of 1 M HCl are added dropwise and the mixture obtained is stirred for ca 10 minutes. A two phase system is obtained and the phases are separated. The organic phase is washed with $H_2O$, dried over $Na_2SO_4$ and the solvent is evaporated off. Solid 1-ethyl-3-nitrosoimidazolidine-2-thion is obtained.

Analogously as described in Example DB 1-methyl-3-nitrosoimidazolidine-2-thion is obtained from 1-methyl-imidazolidine-2-thion, 3-nitroso-1-propyl-imidazolidine-2-thion is obtained from 1-propyl-imidazolidine-2-thion, 4-methyl-1-nitroso-imidazolidine-2-thion is obtained from 4-methyl-imidazolidine-2-thion, and 4,4-dimethyl-1-nitroso-imidazlodine-2-thion is obtained from 4,4-dimethyl-imidazolidine-2-thion.

$^1$H-NMR-Spectra of Compounds (Ex.=Example) in DMSO-d$_6$ if not Otherwise Stated Ex.1: 3.58 and 4.64, AB-quartet, J=18 Hz, 2H, S—CH$_2$; 3.68–4.10, m, 4H, N—CH$_2$; 5.34, d, J=5 Hz, 1H, β-lactam-H; 5.81, d, J=55 Hz, 2H, CH$_2$F; 5.95, dd, J=5 Hz and 8 Hz, 1H, β-lactam-H; 7.87, s, 1H, CH=N; 9.11, b, 1H, NH; 9.85, d, J=8 Hz, 1H, NH.

Ex.2: 3.20–4.28, m, 9H, 4H of N—CH$_2$ and 2H of S—CH$_2$ and 3H of CH$_3$; 5.30, d, J=5 Hz, 1H, β-lactam-H; 5.82, d, J=55 Hz, 2H, CH$_2$F; 5.96, dd, J=5 Hz and J=8 Hz, 1H, β-lactam-H; 7.92, s, 1H, CH=N; 8.34, b, 2H, NH; 8.97, b, 1H, NH; 9.86, d, J=8 Hz, 1H, NH.

Ex.3: 3.52 and 4.54, AB-quartet, j=18 Hz, 2H, S—CH$_2$; 3.67–4.25, m, 4H, N—CH$_2$; 5.29, d, J=5 Hz, 1H, β-lactam-H; 5.79, d, J=55 Hz, 2H, CH$_2$F; 5.93, dd, J=5 Hz and J=8 Hz, 1H, β-lactam-H; 6.85–6.92, m, 3H, CH-aromatic; 7.20–7.30, m, 2H, CH-aromatic; 7.93, s, 1H, CH=N; 8.28, b, 2H, NH; 8.51, b, 1H, NH; 9.84, d, J=8 Hz, 1H, NH.

Ex.4: 2.97, d, J=5 Hz, 3H, CH$_3$, 3.56 and 4.55, AB-quartet, J=18 Hz, 2H, S—CH$_2$; 3.70–4.15, m, 4H, N—CH$_2$; 5.32, d, J=5 Hz, 1H, β-lactam-H; 5.81, d, J=55 Hz, 2H, CH$_2$F, 5.96, dd, J=5 Hz and J=8 Hz, 1H, β-lactam-H; 7.88, s, 1H, CH=N; 8.33, b, 2H, NH; 8.71, d, J=5 Hz, 1H, NH; 9.75, b, 1H, NH; 9.86, d, J=8 Hz, 1H, NH.

Ex.5: 2.83, s, 3H, CH$_3$; 3.00–3.30, m, 6H, N—CH$_2$; 3.40–4.20, m, 7H, 1H of S—CH$_2$ and 6H of N—CH$_2$; 4.44, part of AB-quartet, J=18 Hz, 1H, S—CH$_2$; 5.30, d, J=5 Hz, 1H, β-lactam-H; 5.82, d, J=55 Hz, 2H, CH$_2$F; 5.96, dd, J=5 Hz and J=8 Hz, 1H, β-lactam-H; 7.91, s, 1H, CH=N; 8.34, s, 2H, NH; 9.87, d, J=8 Hz, 1H, NH.

Ex.6: 0.60–0.92, m, 4H, CH$_2$-cycloprop.; 2.50–2.54, m, 1H, CH—C; 3.51 and 4.59, AB-quartet, J=18 Hz, 2H, S—CH$_2$; 3.70–4.10, m, 4H, N—CH$_2$; 5.31, d, J=5 Hz, 1H, β-lactam-H; 5.79, d, J=55 Hz, 2H, CH$_2$F; 5.95, dd, J=5 Hz and J=8 Hz, 1H, β-lactam-H; 7.88, s, 1H, CH=N; 9.85, d, J=8 Hz, 1H, NH.

Ex.7: 3.38–4.18, m, 17H, 16H of N—CH$_2$ and 1H of S—CH$_2$; 4.60, part of AB-quartet, J=18 Hz, 1H, S—CH$_2$; 5.32, d, J=5 Hz, 1H, β-lactam-H; 5.80, d, J=55 Hz, 2H, CH$_2$F; 5.96, dd, J=5 Hz and J=8 Hz, 1H, β-lactam-H; 7.92, s, 1H, H=N; 8.30, b, 2H, NH; 9.86, d, J=8 Hz, 1H, NH.

Ex.8: 3.45–3.70, m, 5H, 4H of N—CH$_2$ and 1H of S—CH$_2$; 3.72–4.10, m, 4H, N—CH$_2$ and O—CH$_2$; 4.59, part of AB-quartet, J=18 Hz, 1H, S—CH$_2$; 5.32, d, J=5 Hz, 1H, β-lactam-H; 5.80, d, J=55 Hz, 2H, CH$_2$F; 5.96, dd, J=5 Hz and J=8 Hz, 1H, β-lactam-H; 7.90, s, 1H, CH=N; 8.33, b, 2H, NH; 9.86, d, J=8 Hz, 1H, NH.

Ex.9: 1.20, t, J=5 Hz, 3H, CH$_3$; 2.90–3.20, m, 4H, N—CH$_2$; 3.40–4.10, m, 7H, 6H von N—CH$_2$ and 1H of S—CH$_2$; 4.60, part of AB-quartet, J=18 Hz, 1H, S—CH$_2$; 5.30, d, J=5 Hz, 1H, β-lactam-H; 5.78, d, J=55 Hz, 2H, CH$_2$F; 5.94, dd, J=5 Hz and J=8 Hz, 1H, β-lactam-H; 7.89, s, 1H, CH=N; 8.28, b, 2H, NH; 9.00, b, 1H, NH; 9.84, d, J=8 Hz, 1H, NH.

Ex.10: 2.85, s, 6H, CH$_3$; 3.35, b, 2H, N—CH$_2$; 3.48–4.15, m, 7H, 6H of N—CH$_2$ and 1H of S—CH$_2$; 4.61, part of AB-quartet, J=18 Hz, 1H, S—CH$_2$; 5.32, d, J=5 Hz, 1H, β-lactam-H; 5.80, d, J=55 Hz, 2H, CH$_2$F; 5.96, dd, J=5 Hz and J=8 Hz, 1H, β-lactam-H; 7.89, s, 1H, CH=N; 8.31, b, 2H, NH; 9.86, d, J=8 Hz, 1H, NH.

Ex.11: 3.05, b, 2H, N—CH$_2$; 3.45–3.68, m, 3H, 2H of N—CH$_2$ and 1H of S—CH$_2$; 3.70–4.15, m, 4H, N—CH$_2$; 4.52, part of AB-quartet, J=18 Hz, 1H, S—CH$_2$; 5.24, d, J=5 Hz, 1H, β-lactam-H; 5.81, d, J=55 Hz, 2H, CH$_2$F; 5.84, dd, J=5 Hz and J=8 Hz, 1H, β-lactam-H; 8.09, s, 1H, CH=N; 8.30, b, 2H, NH; 9.81, d, J=8 Hz, 1H, NH.

Ex.12: 2.90, b, 2H, N—CH$_2$; 3.40–3.61, m, 3H, 2H of O—CH$_2$ and 1H of S—CH$_2$; 3.63–4.20, m, 4H, N—CH$_2$; 4.50, part of AB-quartet, J=18 Hz, 1H, S—CH$_2$; 5.29, d, J=5 Hz, 1H, β-lactam-H; 5.82, d, J=55 Hz, 2H, CH$_2$F; 5.92, dd, J=5 Hz and J=8 Hz, 1H, β-lactam-H; 8.07, s, 1H, CH=N; 8.23, b, 2H, NH; 9.77, d, J=8 Hz, 1H, NH.

Ex.13: 1.72–1.92, m, 2H, CH$_2$; 2.85, b, 2H, N—CH$_2$; 3.38, b, 2H, N—CH$_2$; 3.54 and 4.51, AB-quartet, J=8 Hz, 2H, S—CH$_2$; 3.68–4.14, m, 4H, N—CH$_2$; 5.21, d, J=5 Hz, 1H, β-lactam-H; 5.78, d, J=55 Hz, 2H, CH$_2$F; 5.79, dd, J=5 Hz and J=8 Hz, 1H, β-lactam-H; 8.04, s, 1H, CH=N; 8.26, b, 2H, NH; 9.77, d, J=8 Hz, 1H, NH.

Ex.14: 3.10, b, 2H, N—CH$_2$; 3.20, b, 2H, N—CH$_2$; 3.55 and 4.64, AB-quartet, J=18 Hz, 2H, S—CH$_2$; 3.62–4.15, m, 8H, 6H of N—CH$_2$ and 2H of OCH$_2$; 5.30, d, J=5 Hz, 1H, β-lactam-H; 5.78, d, J=55 Hz, 2H, CH$_2$F; 5.94, dd, J=5 Hz and J=8 Hz, 1H, β-lactam-H; 7.87, s, 1H, CH=N; 9.84, d, J=8 Hz, 1H, NH.

Ex.15: 3.30–4.30, m, 22H, 18H of N—CH$_2$ and 2H of O—CH$_2$ and 2H of S—CH$_2$; 5.25, d, J=5 Hz, 1H, β-lactam-H; 5.79, d, J=55 Hz, 2H, CH$_2$F; 5.75, dd, J=5 Hz and J=8 Hz, 1H, β-lactam-H; 8.15, s, 1H, CH=N; 8.26, b, 2H, NH; 9.77, d, J=8 Hz, 1H, NH.

Ex.16: 1.18–1.50, m, 2H, CH$_2$—C; 1.68–1.98, m, 3H, CH$_2$—C and CH—C; 2.70–2.98, m, 2H, N—CH$_2$; 3.10–3.38, m, 4H, N—CH$_2$; 3.53 and 4.53, AB-quartet, J=18 Hz, 2H, S—CH$_2$; 3.62–4.15, m, 4H, N—CH$_2$; 5.30, d, J=5 Hz, 1H, β-lactam-H; 5.77, d, J=55 Hz, 2H, CH$_2$F; 5.93, dd, J=5 Hz and J=8 Hz, 1H, β-lactam-H; 7.88, s, 1H, CH=N; 9.83, d, J=8 Hz, 1H, NH.

Ex.17: 3.20–4.10, m, 9H, 6H of N—CH$_2$, 1H of S—CH$_2$ and 2H of CH$_2$—C; 4.38, part of AB-quartet, J=18 Hz, 1H, S—CH$_2$; 5.29, d, J=5 Hz, 1H, β-lactam-H; 5.78, d, J=55 Hz, 2H, CH$_2$F; 5.90, dd, J=5 Hz and J=8 Hz, 1H, β-lactam-H; 7.87, s, 1H, CH=N; 7.90–8.20, m, 2H, CH-aromatic; 8.45–8.60, m, 1H, CH-aromatic; 8.78–8.90, m, 1H, CH-aromatic; 9.83, d, J=8 Hz, 1H, NH; 10.17, b, 1H, OH.

Ex.18: 3.40–3.70, m, 9H, 6H of O—CH$_2$ and 2H of N—CH$_2$ and 1H of S—CH$_2$; 3.72–4.12, m, 4H, N—CH$_2$; 4.55, part of AB-quartet, J=18 Hz, 1H, S—CH$_2$; 5.32, d, J=5 Hz, 1H, β-lactam-H; 5.79, d, J=55 Hz, 2H, CH$_2$F; 5.96, dd, J=5 Hz and J=8 Hz, 1H, β-lactam-H; 7.89, s, 1H, CH=N; 9.63, b, 1H, NH; 9.87, d, J=8 Hz, 1H, NH.

Ex.19: 3.50 and 4.45, AB-quartet, J=18 Hz, 2H, S—CH$_2$; 3.70–4.12, m, 4H, N—CH$_2$; 5.28, d, J=5 Hz, 1H, β-lactam-H; 5.78, d, J=55 Hz, 2H, CH$_2$F; 5.93, dd, J=5 Hz and J=8 Hz, 1H, β-lactam-H; 7.84, s, 1H, CH=N; 8.30, b, 2H, NH$_2$; 9.52, b, 1H, NH; 9.83, d, J=8 Hz, 1H, NH; 11.86, b, 1H, OH.

Ex.20: 2.80–3.02, m, 4H, O—CH$_2$; 3.42–4.18, m, 9H, 8H of N—CH$_2$ and 1H of S—CH$_2$; 4.50, part of AB-quartet, J=18 Hz, 1H, S—CH$_2$; 5.31, d, J=5 Hz, 1H, β-lactam-H; 5.78, d, J=55 Hz, 2H, CH$_2$F; 5.94, dd, J=5 Hz and J=8 Hz, 1H, β-lactam-H; 7.86, s, 1H, CH=N; 8.29, b, 2H, NH; 9.32, b, 1H, NH; 9.85, d, J=8 Hz, 1H, NH; 10.16, b, 1H, OH.

Ex.21: 1.59, b, 4H, CH$_2$—C; 2.80, b, 2H, N—CH$_2$; 3.32, b, 2H, N—CH$_2$; 3.53 and 4.53, AB-quartet, J=18 Hz, 2H, S—CH$_2$; 3.68–4.12, m, 4H, N—CH$_2$; 5.24, d, J=5 Hz, 1H, β-lactam-H; 5.81, d, J=55 Hz, 2H, CH$_2$F; 5.80, dd, J=5 Hz and J=8 Hz, 1H, β-lactam-H; 8.05, s, 1H, CH=N; 8.31, b, 2H, NH; 9.80, d, J=8 Hz, 1H, NH.

Ex.22: 3.35, b, 2H, N—CH$_2$; 3.42–3.62, m, 3H, 2H of OCH$_2$ and 1H of S—CH$_2$; 3.65–4.10, m, 4H, N—CH$_2$; 4.46, part of AB-quartet, J=18 Hz, 1H, S—CH$_2$; 5.31, d, J=5 Hz, 1H, β-lactam-H; 5.80, d, J=55 Hz, 2H, CH$_2$F; 5.94, dd, J=5 Hz and J=8 Hz, 1H, β-lactam-H; 7.86, s, 1H, CH=N; 8.30, b, 2H, NH; 9.60, b, 1H, NH; 9.84, d, J=8 Hz, 1H, NH.

Ex.23: 1.28, b, 4H, C—CH$_2$; 1.52, b, 4H, C—CH$_2$; 2.76, b, 2H, N—CH$_2$; 3.25, b, 2H, N—CH$_2$; 3.50 and 4.45, AB-quartet, J=18 Hz, 2H, S—CH$_2$; 3.62–4.10, m, 4H, N—CH$_2$; 5.30, d, J=5 Hz, 1H, β-lactam-H; 5.80, d, J=55 Hz, 2H, CH$_2$F; 5.94, dd, J=5 Hz and J=8 Hz, 1H, β-lactam-H; 7.85, s, 1H, CH=N; 8.10, b, 3H, NH; 8.30, b, 2H, NH; 9.84, d, J=8 Hz, 1H, NH.

Ex.24: 1.25, d, J=5 Hz, 3H, CH$_3$; 3.35–3.68, m, 4H, 2H of N—CH$_2$ and 1H of N—CH and 1H of S—CH$_2$; 3.70–4.20, m, 4H, N—CH$_2$; 4.56, part of AB-quartet, J=18 Hz, 1H, S—CH$_2$; 5.24, d, J=5 Hz, 1H, β-lactam-H; 5.81, d, J=55 Hz, 2H, CH$_2$F; 5.84, dd, J=5 Hz and J=8 Hz, 1H, β-lactam-H; 8.09, s, 1H, CH=N; 8.30, b, 2H, NH; 9.81, d, J=8 Hz, 1H, NH.

Ex.25: 2.92–3.60, m, 5H, 4H of N—CH$_2$ and 1H of S—CH$_2$; 3.62–4.15, m, 12H, 8H of N—CH$_2$ and 4H of O—CH$_2$; 4.35, part of AB-quartet, J=18 Hz, 1H, S—CH$_2$; 5.16, d, J=5 Hz, 1H, β-lactam-H; 5.78, d, J=55 Hz, 2H, CH$_2$F; 5.72, dd, J=5 Hz and J=8 Hz, 1H, β-lactam-H; 8.10, s, 1H, CH=N; 8.25, b, 2H, NH; 9.76, d, J=8 Hz, 1H, NH.

Ex.26: 1.35, s, 6H, CH$_3$; 3.48–4.15, m, 7H, 6H of N—CH$_2$ and 1H of S—CH$_2$; 4.74, part of AB-quartet, J=18 Hz, 1H, S—CH$_2$; 5.32, d, J=5 Hz, 1H, β-lactam-H; 5.81, d, J=55 Hz,. 2H, CH$_2$F; 5.94, dd, J=5 Hz and J=8 Hz, 1H, β-lactam-H; 7.90, s, 1H, CH=N; 9.86, d, J=8 Hz, 1H, NH; 10.26, b, 1H, OH.

Ex.27: 1.16, t, J=7 Hz, 3H, CH$_3$; 3.33, q, J=7 Hz, 2H, CH$_2$; 3.54 and 4.53, AB-quartet, J=18 Hz, 2H, S—CH$_2$; 3.68–4.12, m, 4H, N—CH$_2$; 5.30, d, J=5 Hz, 1H, β-lactam-H; 5.79, d, J=55 Hz, 2H, CH$_2$F; 5.94, dd, J=5 and 8 Hz, 1H, β-lactam-H; 7.87, s, 1H, CH=N; 8.28, b, 2H, NH; 8.68, b, 1H, NH; 9.84, d, J=8 Hz, 1H, NH.

Ex.28: 0.87, t, J=7 Hz, 3H, CH$_3$; 1.55, h, J=7 Hz, 2H, CH$_2$; 3.24, t, J=7 Hz, N—CH$_2$; 3.52 and 4.54, AB-quartet, J=18 Hz, 2H, S—CH$_2$; 3.65–4.12, m, 4H, N—CH$_2$; 5.30, d, J=5 Hz, 1H, β-lactam-H; 5.78, d, J=55 Hz, 2H, CH$_2$F; 5.93, dd, J=5 and 8 Hz, 1H, β-lactam-H; 7.87, s, 1H, CH=N; 8.29, b, 2H, NH; 8.68, b, 1H, NH; 9.84, d, J=8 Hz, 1H, NH.

Ex.29: 2.90–3.05, m, 2H, N—CH$_2$; 3.40–4.18, m, 15H, 6H of N—CH$_2$ and 8H of O—CH$_2$ and 1H of S—CH$_2$; 4.55, part of AB-quartet, J=18 Hz, 1H, S—CH$_2$; 5.33, d, J=5 Hz, 1H, β-lactam-H; 5.80, d, J=55 Hz, 2H, CH$_2$F; 5.95, dd, J=5 and 8 Hz, 1H, β-lactam-H; 7.90, s, 1H, CH=N; 8.26, b, 2H, NH; 8.77, b, 1H, NH; 9.82, d, J=5 Hz, 1H, NH.

Ex.30: 1.72–2.02, m, 2H, CH$_2$; 2.54, s, 3H, N—CH$_3$; 2.94, b, 2H, N—CH$_2$; 3.34–3.64, m, 3H, 2H of N—CH$_2$ and 1H of S—CH$_2$; 3.70–4.10, m, 4H, N—CH$_2$; 4.55, part of AB-quartet, J=18 Hz, 1H, S—CH$_2$; 5.30, d, J=5 Hz, 1H, β-lactam-H; 5.80, d, J=55 Hz, 2H, CH$_2$F; 5.92, dd, J=5 and 8 Hz, 1H, β-lactam-H; 7.87, s, 1H, CH=N; 8.28, b, 2H, NH; 8.88, b, 1H, NH; 9.84, d, J=8 Hz, 1H, NH.

Ex.31: 1.80–2.05, m, 2H, CH$_2$; 2.88–3.12, m, 4H, N—CH$_2$; 3.40, b, 2H, N—CH$_2$; 3.53 and 4.51, AB-quartet, J=18 Hz, 2H, S—CH$_2$; 3.62.–4.12, m, 6H, 4H of N—CH$_2$ and 2H of O—CH$_2$; 5.30, d, J=5 Hz, 1H, β-lactam-H, 5.77, d, J=55 Hz, 2H, CH$_2$F; 5.82, dd, J=5 and 8Hz, 1H, β-lactam-H, 8.03, s, 1H, CH=N; 8.30, b, 2H, NH; 9.80, d, J=8 Hz, 1H, NH.

Ex.32: 1.82–2.10, m, 2H, CH$_2$; 2.75, s, 6H, N—CH$_3$; 3.00–3.18, m, 2H, N—CH$_2$; 3.32–3.48, m, 2H, N—CH$_2$; 3.54 and 4.54, AB-quartet, J=18 Hz, 2H, S—CH$_2$; 3.68–4.12, m, 4H, N—CH$_2$; 5.30, d, J=5 Hz, 1H, β-lactam-H; 5.79, d, J=55 Hz, 2H, CH$_2$F; 5.92, dd, J=5 and 8 Hz, 1H, β-lactam-H; 7.86, s, 1H, CH=N; 8.30, b, 2H, NH; 8.85, b, 1H, NH; 9.84, d, J=8 Hz, 1H, NH.

Ex.33: 1.78–2.02, m, 2H, CH$_2$; 2.95–3.75, m, 11H, 10H of N—CH$_2$ and 1H of S—CH$_2$; 4.10–4.35, m, 2H, O—CH$_2$; 4.65, part of AB-quartet, J=18 Hz, 1H, S—CH$_2$; 5.27, d, J=5 Hz, 1H, β-lactam-H; 5.78, d, J=55 Hz, 2H, CH$_2$F; 5.82, dd, J=5 u 8 Hz, 1H, β-lactam-H; 8.24, b, 2H, 1H of CH=N and 1H of NH; 8.32, b, 1H, NH; 9.77, d, J=8 Hz, 1H, NH.

Ex.34: 1.82–2.02, m, 2H, CH$_2$; 2.55, s, 3H, N—CH$_3$; 2.88–3.02, m, 2H, N—CH$_2$; 3.48–4.22, m, 12H, 8H of N—CH$_2$ and 2H of O—CH$_2$ and 2H of S—CH$_2$; 5.27, d, J=5 Hz, 1H, β-lactam-H; 5.78, d, J=55 Hz, 2H, CH$_2$F; 5.82, dd, J=5 and 8 Hz, 1H, β-lactam-H; 8.10, s, 1H, CH=N; 8.28, b, 2H, NH; 9.78, d, J=8 Hz, 1H, NH.

Ex.35: 1.82–2.08, m, 2H, CH$_2$; 2.85–3.10, m, 4H, N—CH$_2$; 3.38–4.22, m, 14H, 8H, of N—CH$_2$ and 4H of O—CH$_2$ and 2H of S—CH$_2$; 5.17, d, J=5 Hz, 1H, β-lactam-H; 5.80, d, J=55 Hz, 2H, CH$_2$F; 5.82, dd, J=5 and 8 Hz, 1H, β-lactam-H; 8.08, s, 1H, CH=N; 8.27, b, 2H, NH; 9.75, d, J=8 Hz, 1H, NH.

Ex.36: 1.82–2.12, m, 2H, CH$_2$; 2.77, s, 6H, N—CH$_3$; 3.00–3.22, m, 2H, N—CH$_2$; 3.45–4.12, m, 12H, 8H of N—CH$_2$ and 2H of O—CH$_2$ and 2H of S—CH$_2$; 5.20, d, J=5 Hz, 1H, β-lactam-H; 5.82, d, J=55 Hz, 2H, CH$_2$F; 5.85, dd, J=5 and 8 Hz, 1H, β-lactam-H; 8.09, s, 1H, CH=N; 8.30, b, 2H, NH; 9.78, d, J=8 Hz, 1H, NH.

Ex.37: 2.72, s, 6H, N—CH$_3$; 3.42–4.08, m, 9H, 6H of N—CH$_2$ and 2H of O—CH$_2$ and 1H of S—CH$_2$; 4.56, part of AB quartet, J=18 Hz, 1H, S—CH$_2$; 5.30, d, J=5 Hz, 1H, β-lactam-H; 5.79, d, J=55 Hz, 2H, CH$_2$F; 5.94, dd, J=5 and 8 Hz, 1H, β-lactam-H; 7.84, s, 1H, CH=N; 8.24, b, 2H, NH; 9.77, d, J=8 Hz, 1H, NH.

Ex.38: 1.55–1.82, m, 2H, CH$_2$—C; 3.30–3.65, m, 5H, 2H of N—CH$_2$ and 2H of O—CH$_2$ and 1H of S—CH$_2$; 3.70–4.10, m, 4H, N—CH$_2$; 4.51, part of AB-quartet, J=18 Hz, 1H, S—CH$_2$; 5.32, d, J=5 Hz, 1H, β-lactam-H; 5.8, d, J=55 Hz, 2H, CH$_2$F; 5.95, dd, J=5 Hz and 8 Hz, 1H, β-lactam-H; 7.88, s, 1H, CH=N; 8.32, b, 2H, NH; 8.74, m, 1H, OH; 9.73, b, 1H, NH; 9.87, d, J=8 Hz, 1H, NH.

Ex.39: 3.20, d, J=5 Hz, 3H, N—CH$_3$; 3.45–4.05, m, 9H, 6H of N—CH$_2$ and 2H of O—CH$_2$ and 1H of S—CH$_2$; 4.34, part of AB-quartet, J=18 Hz, 1H, S—CH$_2$; 5.29, d, J=5 Hz, 1H, β-lactam-H; 5.78, d, J=55 Hz, 2H, CH$_2$F; 5.95, dd, J=5 Hz and 8 Hz, 1H, β-lactam-H; 7.89, s, 1H, CH=N; 8.33, b, 2H, NH, 8.58, d, J=5 Hz, 1H, NH; 9.86, d, J=8 Hz, 1H, NH.

Ex.40: 2.65–3.05, m, 2H, N—CH$_2$; 3.25–3.45, m, 2H, N—CH$_2$; 3.54 and 4.55, AB-quartet, J=18 Hz, 2H, S—CH$_2$; 3.65–4.12, m, 5H, 4H of N—CH$_2$ and 1H of O—CH; 5.21, d, J=5 Hz, 1H, β-lactam-H; 5.79, d, J=55 Hz, 2H, CH$_2$F; 5.80, dd, J=5 Hz and 8 Hz, 1H, β-lactam-H; 8.05, s, 1H, CH=N; 8.29, b, 2H, NH; 9.78, d, J=8 Hz, 1H, NH.

Ex.41: 2.80–3.20, m, 10H, N—CH$_2$; 3.40–3.65, m, 3H, 1H of S—CH$_2$ and 2H of N-CH$_2$; 3.70–4.05, m, 4H, N—CH$_2$; 4.45, part of AB-quartet, J=18 Hz, 1H, S—CH$_2$; 5.29, d, J=5 Hz, 1H, β-lactam-H; 5.78, d, J=55 Hz, 2H, CH$_2$F; 5.85, d, J=5 Hz, β-lactam-H, 7.93, s, 1H, CH=N.

Ex.42: 1.65–1.92, m, 2H, CH$_2$—C; 3.12–3.32, m, 2H, N—CH$_2$; 3.40–3.58, 3H, 2H of N—CH$_2$ and 1H of S—CH$_2$; 3.62–4.12, m, 4H, N—CH$_2$; 4.55, part of AB-quartet, J=18 Hz, 1H, S—CH$_2$; 5.29, d, J=5 Hz, 1H, β-lactam-H; 5.78, d, J=55 Hz, 2H, CH$_2$F; 5.92, dd, J=5 Hz and 8 Hz, 1H, β-lactam-H; 7.87, s, 1H, CH=N; 9.86, d, J=8 Hz, 1H, NH; 10.01, b, 1H, NH.

Ex.43: 1.20, t, J=7 Hz, 3H, CH$_3$; 3.45–4.22, m, 12H, 8H of N—CH$_2$ and 2H of O—CH$_2$ and 2H of S—CH$_2$; 5.29, d, J=5 Hz, 1H, β-lactam-H; 5.78, d, J=55 Hz, 2H, CH$_2$F; 5.94, dd, J=5 Hz and 8 Hz, 1H, β-lactam-H; 7.91, s, 1H, CH=N; 8.29, b, 2H, NH; 8.61, m, 1H, OH; 9.84, d, J=8Hz, 1H, NH.

Ex.44: 1.82–2.08, m, 4H, CH$_2$—C; 2.82–3.10, m, 6H, N—CH$_2$; 3.35–3.65, m, 3H, 2H of N—CH$_2$ and 1H of S—CH₂; 3.70–4.12, m, 4H, N—CH₂; 4.55, part of AB-quartet, J=18 Hz, 1H, S—CH₂; 5.30, d, J=5 Hz, 1H, β-lactam-H; 5.78, d, J=55 Hz, 2H, CH₂F; 5.94, dd, J=5 Hz and 8 Hz, 1H, β-lactam-H; 8.01, s, 1H, CH=N; 8.30, b, 2H, NH; 9.78, d, J=8 Hz, 1H, NH.

Ex.45: 1.30–1.70, m, 4H, CH₂—C; 1.85–2.10, m, 4H, CH₂—C; 2.85–3.10, m, 1H, CH—C; 3.40–3.55, m, 2H, 1H of CH and 1H of S—CH₂; 3.56–4.10, m, 4H, N—CH₂; 4.59, part of AB-quartet, J=18 Hz, 1H, S—CH₂; 5.29, d, J=5 Hz, 1H, β-lactam-H; 5.78, d, J=55 Hz, 2H, CH₂F; 5.94, dd, J=5 Hz and 8 Hz, 1H, β-lactam-H; 7.85, s, 1H, CH=N; 8.30, b, 6H, NH; 9.88, d, J=5 Hz, 1H, NH; 10.01, b, 1H, NH.

Ex.46: 1.15, t, J=7 Hz, 3H, CH₃; 3.40–3.62, m, 3H, 2H of CH₂ and 1H of S—CH₂; 3.70–4.10, m, 4H, N—CH₂; 4.55, part of AB-quartet, J=8 Hz, 1H, S—CH₂; 5.29, d, J=5 Hz, 1H, β-lactam-H; 5.81, d, J=55 Hz, 2H, CH₂F; 5.94, dd, J=5 Hz and 8 Hz, 1H, β-lactam-H; 7.85, s, 1H, CH=N; 8.30, b, 2H, NH; 9.83, d, J=8Hz, 1H, NH.

Ex.47: 3.20–4.10, m, 10H, 6H of N—CH₂ and 2H of O—CH₂ and 1H of O—CH and 1H of S—CH₂; 4.55, part of AB-quartet, J=18 Hz, 1H, S—CH₂; 5.30, d, J=5 Hz, 1H, β-lactam-H; 5.81, d, J=55 Hz, 2H, CH₂F; 5.94, dd, J=5 Hz and 8 Hz, 1H, β-lactam-H; 7.87, s, 1H, CH=N; 8.28, b, 2H, NH; 8.68, b, 1H, OH; 9.47, b, 1H, OH; 9.84, d, J=8 Hz, 1H, NH.

Ex.48: 1.18, t, J=7 Hz, 3H, CH₃; 3.16, d, J=5 Hz, 3H, N—CH₃; 3.45–3.68, m, 3H, 2H of N—CH₂ and 1H of S—CH₂; 3.70–4.10, m, 4H, N—CH₂; 4.29, part of AB-quartet, J=18 Hz, 1H, S—CH₂; 5.29, d, J=5 Hz, 1H, β-lactam-H; 5.81, d, J=55 Hz, 2H, CH₂F; 5.96, dd, J=5 Hz and 8 Hz, 1H, β-lactam-H; 7.87, s, 1H, CH=N; 8.29, b, 2H, NH; 8.66, d, J=5 Hz, 1H, NH; 9.84, d, J=8 Hz, 1H, NH.

Ex.49: 1.16, t, J=7 Hz, 3H, CH₃; 1.88–2.10, m, 2H, CH₂—C; 2.78, s, 6H, N—CH₃; 3.00–3.20, m, 2H, N—CH₂; 3.40–4.20, m, 10H, 8H of N—CH₂; 2H of S—CH₂; 5.17, d, J=5 Hz, 1H, β-lactam-H; 5.80, d, J=55 Hz, 2H, CH₂F; 5.82, dd, J=5 Hz and 8 Hz, 1H, β-lactam-H; 8.05, s, 1H, CH=N; 8.28, b, 2H, NH; 9.74, d, J=8 Hz, 1H, NH.

Ex.50: 1.20, t, J=7 Hz, 3H, CH₃; 1.75–2.00, m, 2H, CH₂—C; 2.90–3.60, m, 9H, 8H, of N—CH₂ and 1H of S—CH₂; 4.08–4.38, m, 2H, N—CH₂; 4.65, part of AB-quartet, J=18 Hz, 1H, S—CH₂; 5.28, d, J=5 Hz, 1H, β-lactam-H; 5.78, d, J=55 Hz, 2H, CH₂F; 5.84, dd, J=5 Hz and 8 Hz, 1H, β-lactam-H; 8.24, b, 2H, 1H of CH=N and 1H of NH; 8.37, b, 1H, NH; 9.77, d, J=8 Hz, 1H, NH.

Ex.51: 1.14, t, J=7 Hz, 3H, CH₃; 1.30–1.75, m, 4H, CH₂—C; 1.88–2.12, m, 4H, CH₂—C; 2.88–3.10, m, 1H, N—CH; 3.40–4.22, m, 9H, 6H of N—CH₂ and 1H of N—CH and 2H of S—CH₂; 5.28, d, J=5 Hz, 1H, β-lactam-H; 5.78, d, J=55 Hz, 2H, CH₂F; 5.94, dd, J=5 Hz and 8 Hz, 1H, β-lactam-H; 7.93, s, 1H, CH=N; 8.27, b, 5H, NH; 9.85, d, J=8 Hz, 1H, NH.

Ex.52: 1.25–1.70, m, 4H, CH₂—C; 1.85–2.12, m, 4H, CH₂—C; 2.88–3.10, m, 1H, N—CH; 3.45–4.28, m, 11H, 6H of N—CH₂ and 1H of N—CH and 2H of O—CH₂ and 2H of S—CH₂; 5.15, d, J=5 Hz, 1H, β-lactam-H; 5.81, d, J=55 Hz, 2H, CH₂F; 5.74, dd, J=5 Hz and 8 Hz, 1H, β-lactam-H; 8.18, b, 3H, 1H of CH=N and 2H of NH; 8.28, b, 3H, NH; 9.79, d, J=8 Hz, 1H, NH.

Ex.53: 2.72–2.92, m, 2H, CH₂—C; 3.10–3.30, m, 6H, N—CH₂; 3.32–3.60, m, 3H, 2H of N—CH₂ and 1 H of S—CH₂; 3.62–4.15, m, 8H, NCH₂; 4.59, part of AB-quartet, J=18 Hz, 1H, S—CH₂; 5.29, d, J=5 Hz, 1H, β-lactam-H; 5.81, d, J=55 Hz, 2H, CH₂F; 5.94, dd, J=5 Hz and 8 Hz, 1H, β-lactam-H; 7.86, s, 1H, CH=N; 8.08, b, 2H, NH; 8.28, b, 2H, NH; 8.59, b, 1H, NH; 8.96, b, 1H, NH; 9.84, d, J=8 Hz, 1H, NH.

Ex.54: 1.70–1.92, m, 2H, CH₂—C; 2.76, d, J=4 Hz, 6H, N—CH₃; 3.10–3.25, m, 2H, N—CH₂; 3.27–3.42, m, 2H, N—CH₂; 3.41 and 4.51, AB-quartet, J=18 Hz, 2H, S—CH₂; 3.70–4.10, m, 4H, N—CH₂; 5.17, d, J=5 Hz, 1H, β-lactam-H; 5.73, dd, J=5 Hz and 8 Hz, 1H, β-lactam-H; 5.78, d, J=55 Hz, 2H, CH₂F; 7.72, b, 2H, NH; 8.04, s, 1H, CH=N; 8.26, b, 2H, NH; 8.60, b, 1H, NH; 9.76, d, J=8 Hz, 1H, NH.

Ex.55: 3.04, s, 3H, N—CH₃; 3.53 and 4.54, AB-quartet, J=18 Hz, 2H, S—CH₂; 3.68–4.04, m, 4H, N—CH₂; 5.29, d, J=5 Hz, 1H, β-lactam-H; 5.79, d, J=55 Hz, 2H, CH₂F; 5.94, dd, J=5 Hz and 8 Hz, 1H, β-lactam-H; 7.85, s, 1H, CH=N; 8.29, b, 2H, NH; 9.83, d, J=8 Hz, 1H, NH.

Ex.56: 3.16, s, 3H, N—CH₃; 3.17, s, 3H, N—CH₃; 3.57 and 4.32, AB-quartet, J=18 Hz, 2H, S—CH₂; 3.68–4.08, m, 4H, N—CH₂; 5.29, d, J=5 Hz, 1H, β-lactam-H; 5.78, d, J=55 Hz, 2H, CH₂F; 5.95, dd, J=5 Hz and 8 Hz, 1H, β-lactam-H; 7.86, s, 1H, CH=N; 8.30, b, 2H, NH; 8.64, b, 1H, NH; 9.84, d, J=8 Hz, 1H, NH.

Ex.57: 1.21, t, J=7 Hz, 3H, CH₃; 3.10, s, 3H, N—CH₃; 3.48–4.10, m, 7H, 6H of N—CH₂ and 1H of S—CH₂; 4.20, part of AB-quartet, J=18 Hz, 1H, S—CH₂; 5.29, d, J=5 Hz, 1H, β-lactam-H; 5.79, d, J=55 Hz, 2H, CH₂F; 5.95, dd, J=5 Hz and 8 Hz, 1H, β-lactam-H; 7.89, s, 1H, CH=N; 8.30, b, 2H, NH; 8.69, b, 1H, NH; 9.84, d, J=8 Hz, 1H, NH.

Ex.58: 1.30–1.75, m, 4H, CH₂—C; 1.88–2.12, m, 4H, CH₂—C; 2.85–3.02, m, 1H, N—CH; 3.07, s, 3H, CH₃; 3.45–4.21, m, 7H, 4H of N—CH₂ and 1H of N—CH and 2H of S—CH₂; 5.28, d, J=5 Hz, 1H, β-lactam-H; 5.80, d, J=55 Hz, 2H, CH₂F; 5.94, dd, J=5 Hz and 8 Hz, 1H, β-lactam-H; 7.91, s, 1H, CH=N; 8.31, b, 3H, NH; 9.85, d, J=8 Hz, 1H, NH.

Ex.59: 3.14, s, 3H, CH₃; 3.50–4.10, m, 9H, 6H of N—CH₂ and 2H of O—CH₂ and 1H of S—CH₂; 4.25, part of AB-quartet, J=18 Hz, 1H, S—CH₂; 5.29, d, J=5 Hz, 1H, β-lactam-H; 5.79, d, J=55 Hz, 2H, CH₂F; 5.94, dd, J=5 Hz and 8 Hz, 1H, β-lactam-H; 7.89, s, 1H, CH=N; 8.23, b, 2H, NH; 9.75, d, J=8 Hz, 1H, NH.

Ex.60: 3.48–4.10, m, 13H, 8H of N—CH₂ and 4H of O—CH₂ and 1H of S—CH₂; 4.20, part of AB-quartet, J=18 Hz, 1H, S—CH₂; 5.13, d, J=5 Hz, 1H, β-lactam-H; 5.72, dd, J=5 Hz and 8 Hz, 1H, β-lactam-H; 5.79, d, J=55 Hz, 2H, CH₂F; 8.16, s, 1H, CH=N; 8.24, b, 2H, NH; 9.76, d, J=8 Hz, 1H, NH.

Ex.61: 1.24, t, J=7 Hz, 6H, CH₃; 3.05–3.45, m, 6H, N—CH₂; 3.54 and 4.55, AB-quartet, J=18 Hz, 2H, S—CH₂; 3.70–4.10, m, 6H, N—CH₂; 5.29, d, J=5 Hz, 1H, β-lactam-H; 5.80, d, J=55 Hz, 2H, CH₂F; 5.96, dd, J=5 Hz and 8 Hz, 1H, β-lactam-H; 7.86, s, 1H, CH=N; 8.28, b, 2H, NH; 9.83, d, J=8 Hz, 1H, NH; 10.89, b, 1H, NH.

Ex.62: 1.90–2.14, m, 2H, CH₂—C; 2.73, d, J=4 Hz, 6H, N—CH₃; 3.00–3.20, m, 2H, N—CH₂; 3.32–4.10, m, 7H, 6H of N—CH₂ and 1H of S—CH₂; 4.60, part of AB-quartet, J=18 Hz, 1H, S—CH₂; 5.30, d, J=5 Hz, 1H, β-lactam-H; 5.79, d, J=55 Hz, 2H, CH₂F; 5.94, dd, J=5 Hz and 8 Hz, 1H, β-lactam-H; 7.86, s, 1H, CH=N; 8.30, b, 2H, NH; 9.83, d, J=8 Hz, 1H, NH; 10.97, b, 1H, NH.

Ex.63: 1.24, t, J=7 Hz, 6H, CH₃; 3.05–3.40, m, 6H, N—CH₂; 3.53 and 4.56, AB-quartet, J=18 Hz, 2H, S—CH₂; 3.70–4.18, m, 6H, N—CH₂; 5.30, d, J=5 Hz, 1H, β-lactam-H; 5.79, d, J=55 Hz, 2H, CH₂F; 5.94, dd, J=5 Hz and 8 Hz, 1H, β-lactam-H; 7.87, s, 1H, CH=N; 8.28, b, 2H, NH; 9.02, b, 1H, NH; 9.84, d, J=8 Hz, 1H, NH; 10.26, b, 1H, NH; 10.89, b, 1H, NH.

Ex.64: 1.21, t, J=7 Hz, 6H, CH₃; 3.08–3.30, m, 7H, 4H of N—CH₂ and 3H of N—CH₃; 3.32–3.50, m, 2H, N—CH₂;

3.58 and 4.24, AB-quartet, J=18 Hz, 2H, S—CH$_2$; 3.75–4.10, m, 6H, N—CH$_2$; 5.12, d, J=5 Hz, 1H, β-lactam-H; 5.70, dd, J=5 Hz and 8 Hz, 1H, β-lactam-H; 5.78, d, J=55 Hz, 2H, CH$_2$F; 8.15, s, 1H, CH=N; 8.23, b, 2H, NH; 9.75, d, J=8 Hz, 1H, NH.

Ex.65: 2.79, d, J=4 Hz, 6H, N—CH$_3$; 3.32–3.48, m, 2H, N—CH$_2$; 3.53 and 4.56, AB-quartet, J=18 Hz, 2H, S—CH$_2$; 3.68–4.04, m, 6H, N—CH$_2$; 5.30, d, J=5 Hz, 1H, β-lactam-H; 5.78, d, J=55 Hz, 2H, CH$_2$F; 5.94, dd, J=5 Hz and 8 Hz, 1H, β-lactam-H; 7.86, s, 1H, CH=N; 8.28, b, 2H, NH; 9.84, d, J=8 Hz, 1H, NH; 10.95, b, 1H, NH.

Ex.66 (in DMSO-d$_6$/CF$_3$COOD): 3.50 and 4.31, AB-quartet, J=18 Hz, 2H, S—CH$_2$; 3.75–4.20, m, 4H, N—CH$_2$; 5.17, s, 2H, OCH$_2$; 5.29, d, J=5 Hz, 1H, β-lactam-H; 5.79, d, J=55 Hz, 2H, CH$_2$F; 5.94, dd, J=5 Hz and 8 Hz, 1H, β-lactam-H; 7.33, s, 1H, CH; 7.87, s, 1H, CH=N; 8.32, s, 1H, CH; 9.84, d, J=8 Hz, 1H, NH.

Ex.67: 1.10–2.20, m, 8H, CH$_2$—C; 3.12–3.40, m, 1H, N—CH; 3.55 and 4.55, AB-quartet, J=18 Hz, 2H, S—CH$_2$; 3.65–4.18, m, 5H, 4H of N—CH$_2$ and 1H of N—CH; 5.23, d, J=5 Hz, 1H, β-lactam-H; 5.79, d, J=55 Hz, 2H, CH$_2$F; 5.84, dd, J=5 Hz and 8 Hz, 1H, β-lactam-H; 8.10, s, 1H, CH=N; 8.27, b, 3H, NH; 9.82, d, J=8 Hz, 1H, NH.

Ex.68: 1.10–2.20, m, 8H, CH$_2$—C; 3.18–3.40, m, 1H, N—CH, 3.55 and 4.59, AB-quartet, J=18 Hz, 2H, S—CH$_2$; 3.68–4.20, m, 5H, 4H of N—CH$_2$ and 1H of N—CH; 5.21, d, J=5 Hz, 1H, β-lactam-H; 5.78, d, J=55 Hz, 2H, CH$_2$F; 5.80, dd, J=5 Hz and 8 Hz, 1H, β-lactam-H; 8.07, s, 1H, CH=N; 8.26, b, 3H, NH; 9.77, d, J=8 Hz, 1H, NH.

Ex.69: 0.88, t, J=7 Hz, 3H, CH$_3$; 1.40–1.70, m, 2H, CH$_2$—C; 3.30–3.48, m, 2H, N—CH$_2$; 3.53 and 4.55, AB-quartet, J=18 Hz, 2H, S—CH$_2$; 3.65–4.08, m, 4H, N—CH$_2$; 5.29, d, J=5 Hz, 1H, β-lactam-H; 5.79, d, J=55 Hz, 2H, CH$_2$F; 5.93, dd, J=5 Hz and 8 Hz, 1H, β-lactam-H; 7.85, s, 1H, CH=N; 8.29, b, 2H, NH; 9.84, d, J=8 Hz, 1H, NH.

Ex.70: 0.90, t, J=7 Hz, 3H, CH$_3$; 1.48–1.72, m, 2H, CH$_2$—C; 3.16, d, J=5 Hz, 3H, N—CH$_3$; 3.32–3.50, m, 2H, N—CH$_2$; 3.58 and 4.25, AB-quartet, J=18 Hz, 2H, S—CH$_2$; 3.70–4.10, m, 4H, N—CH$_2$; 5.28, d, J=5 Hz, 1H, β-lactam-H; 5.79, d, J=55 Hz, 2H, CH$_2$F; 5.94, dd, J=5 Hz and 8 Hz, 1H, β-lactam-H; 7.87, s, 1H, CH=N; 8.29, b, 2H, NH; 8.71, d, J=5 Hz, 1H, NH; 9.84, d, J=8 Hz, 1H, NH.

Ex.71: 1.00–1.44, m, 12H, CH$_3$; 3.54 and 4.59, AB-quartet, J=18 Hz, 2H, S—CH$_2$; 3.75–4.30, m, 6H, 4H of N—CH$_2$ and 2H of N—CH; 5.32, d, J=5 Hz, 1H, β-lactam-H; 5.80, d, J=55 Hz, 2H, CH$_2$F; 5.98, dd, J=5 Hz and 8 Hz, 1H, β-lactam-H; 8.00, s, 1H, CH=N; 8.30, b, 2H, NH; 9.53, b, 1H, NH; 9.86, d, J=8 Hz, 1H, NH; 10.39, b, 1H, NH; 10.78, b, 1H, NH.

Ex.72: 1.19, d, J=7 Hz, 6H, CH$_3$; 3.53 and 4.55, AB-quartet, J=18 Hz, 2H, S—CH$_2$; 3.65–4.02, m, 4H, N—CH$_2$; 4.15–4.32, m, 1H, N—CH; 5.29, d, J=5 Hz, 1H, β-lactam-H; 5.80, d, J=55 Hz, 2H, CH$_2$F; 5.94, dd, J=5 Hz and 8 Hz, 1H, β-lactam-H; 7.85, s, 1H, CH=N; 8.28, b, 2H, NH; 9.83, d, J=8 Hz 1H, NH.

Ex.73: 1.30–1.90, m, 6H, CH$_2$—C; 2.82–3.05, m, 2H, N—CH$_2$; 3.24–3.65, 5H, 4H of N—CH$_2$ and 1H of S—CH$_2$; 3.75–4.10, m, 6H, N—CH$_2$; 4.58, part of AB-quartet, J=18 Hz, 1H, S—CH$_2$; 5.30, d, J=5 Hz, 1H, β-lactam-H; 5.80, d, J=55 Hz, 2H, CH$_2$F; 5.94, dd, J=5 Hz and 8 Hz, 1H, β-lactam-H; 7.85, s, 1H, CH=N; 8.29, b, 2H, NH; 9.84, d, J=8 Hz, 1H, NH; 10.95, b, 1H, NH.

Ex.74: 0.90, t, J=7 Hz, 3H, CH$_3$; 1.25–1.42, m, 2H, CH$_2$—C; 1.50–1.70, m, 2H, CH$_2$—C; 3.16, d, J=5 Hz, 3H, N—CH$_3$; 3.40–3.50, m, 2H, N—CH$_2$; 3.58 and 4.25, AB-quartet, J=18 Hz, 2H, S—CH$_2$; 3.70–4.12, m, 4H, N—CH$_2$; 5.29, d, J=5 Hz, 1H, β-lactam-H; 5.78, d, J=55 Hz, 2H, CH$_2$F; 5.94, dd, J=5 Hz and 8 Hz, 1H, β-lactam-H; 7.87, s, 1H, CH=N; 8.29, b, 2H, NH; 8.69, d, J=5 Hz, 1H, NH; 9.84, d, J=8 Hz, 1H, NH.

Ex.75: 0.90, t, J=7 Hz, 3H, CH$_3$; 1.20–1.40, m, 2H, CH$_2$—C; 1.45–1.65, m, 2H, CH$_2$—C; 3.35–3.50, m, 2H, N—CH$_2$; 3.53 and 4.55, AB-quartet, J=18 Hz, 2H, S—CH$_2$; 3.70–4.10, m, 4H, N—CH$_2$; 5.30, d, J=5 Hz, 1H, β-lactam-H; 5.79, d, J=55 Hz, 2H, CH$_2$F; 5.94, dd, J=5 Hz. and 8 Hz, 1H, β-lactam-H; 7.85, s, 1H, CH=N; 8.29, b, 2H, NH; 9.84, d, J=8 Hz, 1H, NH.

Ex.76: 1.30–1.90, m, 6H, CH$_2$—C; 2.85–3.08, m, 2H, N—CH$_2$; 3.20, d, J=5 Hz, 3H, N—CH$_3$; 3.30–3.70, m, 5H, 4H of N—CH$_2$ and 1H of S—CH$_2$; 3.75–4.10, m, 6H, N—CH$_2$; 4.21, part of AB-quartet, J=18 Hz, 1H, S—CH$_2$; 5.28, d, J=5 Hz, 1H, β-lactam-H; 5.79, d, J=55 Hz, 2H, CH$_2$F; 5.94, dd, J=5 Hz and 8 Hz, 1H, β-lactam-H; 7.88, s, 1H, CH=N; 8.26, b, 2H, NH; 9.11, d, J=5 Hz, 1H, NH; 9.84, d, J=8 Hz, 1H, NH.

Ex.77: 1.78–2.10, m, 4H, CH$_2$—C; 3.00–3.20, m, 2H, N—CH$_2$; 3.40–3.65, m, 5H, 4H of N—CH$_2$ and 1H of S—CH$_2$; 3.80–4.10, m, 6H, N—CH$_2$; 4.59, part of AB-quartet, J=18 Hz, 1H, β-lactam-H; 5.30, d, J=5 Hz, 1H, β-lactam-H; 5.80, d, J=55 Hz, 2H, CH$_2$F; 5.93, dd, J=5 Hz and 8 Hz, 1H, β-lactam-H; 7.86, s, 1H, CH=N; 8.28, b, 2H, NH; 9.84, d, J=8 Hz, 1H, NH.

Ex.78: 3.54 and 4.54, AB-quartet, J=18 Hz, 2H, S—CH$_2$; 3.62–4.18, m, 4H, N—CH$_2$; 4.34, s, 2H, N—CH$_2$; 5.33, d, J=5 Hz, 1H, β-lactam-H; 5.81, d, J=55 Hz, 2H, CH$_2$F; 5.96, dd, J=5 Hz and 8 Hz, 1H, β-lactam-H; 7.93, s, 1H, CH=N; 8.30, b, 2H, NH; 9.86, d, J=8 Hz, 1H, NH.

Ex.79: 0.87, t, J=7 Hz, 3H, CH$_3$; 1.18–1.40, m, 4H, CH$_2$—C; 1.42–1.68, m, 2H, CH$_2$—C; 3.30–3.50, 2H, N—CH$_2$; 3.53 and 4.54, AB-quartet, J=18 Hz, 2H, S—CH$_2$; 3.70–4.10, m, 4H, N—CH$_2$; 5.30, d, J=5 Hz, 1H, β-lactam-H; 5.79, d, J=55 Hz, 2H, CH$_2$F; 5.94, dd, J=5 Hz and 8 Hz, 1H, β-lactam-H; 7.85, s, 1H, CH=N; 8.26, b, 2H, NH; 8.70, b, 2H, NH; 9.83, d, J=8 Hz, 1H, NH.

Ex.80: 0.86, t, J=7 Hz, 3H, CH$_3$; 1.20–1.40, m, 6H, CH$_2$—C; 1.42–1.70, m, 2H, CH$_2$—C; 3.38–3.51, m, 2H, N—CH$_2$; 3.54 and 4.54, AB-quartet, J=18 Hz, 2H, S—CH$_2$; 3.70–4.10, m, 4H, N—CH$_2$; 5.30, d, J=5 Hz, 1H, β-lactam-H; 5.79, d, J=55 Hz, 2H, CH$_2$F; 5.93, dd, J=5 Hz and 8 Hz, 1H, β-lactam-H; 7.86, s, 1H, CH=N; 8.25, b, 2H, NH; 8.77, b, 2H, NH; 9.79, d, J=8 Hz, 1H, NH.

Ex.81: 0.85, t, J=7 Hz, 3H, CH$_3$; 1.12–1.38, m, 8H, CH$_2$—C; 1.40–1.68, m, 2H, CH$_2$—C; 3.35–3.62, m, 3H, 2H of N—CH$_2$ and 1H of S—CH$_2$; 3.70–4.10, m, 4H, N—CH$_2$; 4.55, Part of AB-quartet, J=18 Hz, 1H, S—CH$_2$; 5.30, d, J=5 Hz, 1H, β-lactam-H; 5.79, d, J=55 Hz, 2H, CH$_2$F; 5.93, dd, J=5 Hz and 8 Hz, 1H, β-lactam-H; 7.85, s, 1H, CH=N; 8.27, b, 2H, NH; 9.84, d, J=8 Hz, 1H, NH.

Ex.82: 3.50–3.78, m, 5H, 4H of N—CH$_2$ and 1H of S—CH$_2$; 4.00–4.48, m, 5H, 4H of N—CH$_2$ and 1H of S—CH$_2$; 5.32, d, J=5 Hz, 1H, β-lactam-H; 5.79, d, J=55 Hz, 2H, CH$_2$F; 5.94, dd, J=5 Hz and 8 Hz, 1H, β-lactam-H; 7.90, s, 1H, CH=N; 8.28, b, 2H, NH; 9.83, d, J=8 Hz, 1H, NH; 10.07, b, 1H, NH.

Ex.83: 1.90–2.05, m, 2H, CH$_2$—C; 3.28–3.46, m, 4H, N—CH$_2$; 3.54 and 4.45, AB-quartet, J=18 Hz, 2H, S—CH$_2$; 3.68–4.10, m, 4H, N—CH$_2$; 5.31, d, J=5 Hz, 1H, β-lactam-H; 5.79, d, J=55 Hz, 2H, CH$_2$F; 5.94, dd, J=5 Hz and 8 Hz, 1H, β-lactam-H; 7.87, s, 1H, CH=N; 8.30, b, 2H, NH; 9.26, b, 1H, NH; 9.84, d, J=8 Hz, 1H, NH.

Ex.84: 1.10–1.30, m, 12H, CH$_3$; 3.17, d, J=5 Hz, 3H, N—CH$_3$; 3.48–3.70, m, 3H, 2H of N—CH$_2$ and 1H v S—CH$_2$; 3.75–4.00, m, 4H, N—CH$_2$; 4.37, part of AB-quartet, J=18 Hz, 1H, S—CH$_2$; 5.32, d, J=5 Hz, 1H, β-lactam-H; 5.65, part of dublet, 1H, CH$_2$F; 5.80–6.08, m, 4H, 1H of CH$_2$F and 1H of β-lactam-H and 2H of O—CH$_2$; 7.79, s, 1H, CH=N; 8.44, b, 1H, NH; 8.65, d, J=5 Hz, 1H, NH; 9.86, d, J=8 Hz, 1H, NH.

Ex.85: 1.21, t, J=7 Hz, 3H, CH$_3$; 3.14, s, 6H, N—CH$_3$; 3.30–3.55, q, J=7 Hz, 2H, N—CH$_2$; 3.61, part of AB-quartet, J=18 Hz, 1H, S—CH$_2$; 3.70–4.20, m, 5H, 4H of N—CH$_2$ and 1H of S—CH$_2$; 5.28, d, J=5 Hz, 1H, β-lactam-H; 5.79, d, J=55 Hz, 2H, CH$_2$F; 5.95, dd, J=5 Hz and 8 Hz, 1H, β-lactam-H; 7.94, s, 1H, CH=N; 8.31, b, 2H, NH; 9.84, d, J=8 Hz, 1H, NH.

Ex.86: 3.12, s 3H, N—CH$_3$, 3.14, s, 6H, N—CH$_3$; 3.61, Part of AB-quartet, J=18 Hz, 1H, S—CH$_2$; 3.70–4.18, m, 5H, 4H of N—CH$_2$ and 1H of S—CH$_2$; 5.29, d, J=5 Hz, 1H, β-lactam-H; 5.79, d, J=55 Hz, 2H, CH$_2$F; 5.94, dd, J=5 Hz and 8 Hz, 1H, β-lactam-H; 7.92, s, 1H, CH=N; 8.32, b, 2H, NH; 9.84, d, J=8 Hz, 1H, NH.

Ex.87: 1.12–1.30, m, 6H, CH$_3$; 3.09, s, 3H, N—CH$_3$; 3.32–4.20, m, 10H, 8H of N—CH$_2$ and 2H of S—CH$_2$; 5.28, d, J=5 Hz, 1H, β-lactam-H; 5.78, d, J=55 Hz, 2H, CH$_2$F; 5.95, dd, J=5 Hz and 8 Hz, 1H, β-lactam-H; 7.95, s, 1H, CH=N; 8.31, b, 2H, NH; 9.84, d, J=8 Hz, 1H, NH.

Ex.88: 0.92, t, J=7 Hz, 3H, CH$_3$; 1.50–1.75, m, 2H, CH$_2$—C; 3.14, s, 6H, N—CH$_3$; 3.30–3.50, m, 2H, N—CH$_2$; 3.61, part of AB-quartet, J=18 Hz, 1H, S—CH$_2$; 3.72–4,18, m, 5H, 4H of N—CH$_2$ and 1H of S—CH$_2$; 5.29, d, J=5 Hz, 1H, β-lactam-H; 5.80, d, J=55 Hz, 2H, CH$_2$F; 5.94, dd, J=5 Hz and 8 Hz, 1H, β-lactam-H; 7.94, s, 1H, CH=N; 8.30, b, 2H, NH; 9.84, d, J=8 Hz, 1H, NH.

Ex.89: 3.28, s, 3H, N—CH$_3$; 3.42–3.72, m, 5H, 4H of N—CH$_2$ and 1H of S—CH$_2$; 3.90–4.50, m, 5H, 4H of N—CH$_2$ and 1H of S—CH$_2$; 5.29, d, J=5 Hz, 1H, β-lactam-H; 5.80, d, J=55 Hz, 2H, CH$_2$F; 5.95, dd, J=5 Hz and 8 Hz, 1H, β-lactam-H; 7.91, s, 1H, CH=N; 8.30, b, 2H, NH; 9.85, d, J=8 Hz, 1H, NH.

Ex.90: 1.90–2.12, m, 2H, CH$_2$—C; 3.20–3.60, m, 8H, 4H of N—CH$_2$ and 3H of N—CH$_3$ and 1H of S—CH$_2$; 3.62–4.15, m, 5H, 4H of N—CH$_2$ and 1H of S—CH$_2$; 5.27, d, J=5 Hz, 1H, β-lactam-H; 5.79, d, J=55 Hz, 2H, CH$_2$F; 5.94, dd, J=5 Hz and 8 Hz, 1H, β-lactam-H; 7.91, s, 1H, CH=N; 8.31, b, 2H, NH; 9.84, d, J=8 Hz, 1H, NH.

Ex.91 (diaisostereomeric mixture): 1.20–1.40, m, 3H, CH$_3$; 3.30–3.65, m, 2H, 1H of N—CH and 1H of S—CH$_2$; 3.95–4.30, m, 2H, N—CH$_2$; 4.53, part of AB-quartet, J=18 Hz, 1H, S—CH$_2$; 5.30, d, J=5 Hz, 1H, β-lactam-H; 5.79, d, J=55 Hz, 2H, CH$_2$F; 5.93, dd, J=5 Hz and 8 Hz, 1H, β-lactam-H; 7.83, s, 1H, CH=N; 9.27, b, 1H, NH; 9.84, d, J=8 Hz, 1H, NH.

Ex.92 (diaisostereomeric mixture): 1.20–1.40, m, 3H, CH$_3$; 2.94, d, J=5 Hz, 3H, N—CH$_3$; 3.30–3.70, m, 2H, 1H of N—CH and 1H of S—CH$_2$; 3.90–4.30, m, 2H, N—CH$_2$; 4.49, part of AB-quartet, J=18 Hz, 1H, S—CH$_2$; 5.31, d, J=5 Hz, 1H, β-lactam-H; 5.79, d, J=55 Hz, 2H, CH$_2$F; 5.94, dd, J=5 Hz and 8 Hz, 1H, β-lactam-H; 7.83, s, 1H, CH=N; 8.30, b, 2H, NH; 8.65, d, J=5 Hz, 1H, NH; 9.84, d, J=8 Hz, 1H, NH.

Ex.93: 1.32, d, J=6 Hz, 3H, CH$_3$; 1.70–1.98, m, 2H, CH$_2$—C; 2.75–2.98, m, 2H, N—CH$_2$; 3.25–3.65, m, 4H, 2H of N—CH$_2$ and 1H of N—CH and 1H of S—CH$_2$; 4.05–4.35, m, 2H, N—CH$_2$; 4.53, part of AB-quartet, J=18 Hz, 1H, S—CH$_2$; 5.22, d, J=5 Hz, 1H, β-lactam-H; 5.78, d, J=55 Hz, 2H, CH$_2$F; 5.80, dd, J=5 Hz and 8 Hz, 1H, β-lactam-H; 8.01, s, 1H, CH=N; 8.28, b, 2H, NH; 9.78, d, J=8 Hz, 1H, NH.

Ex.94: 1.28, d, J=6 Hz, 3H, CH$_3$; 1.70–1.92, m, 2H, CH$_2$—C; 2.72–3.00, m, 2H, N—CH$_2$; 3.22–3.72, m, 4H, 2H of N—CH$_2$ and 1H of N—CH and 1H of S—CH$_2$; 3.90–4.35, m, 2H, N—CH$_2$; 4.49, part of AB-quartet, J=18 Hz, 1H, S—CH$_2$; 5.19, d, J=5 Hz, 1H, β-lactam-H; 5.76, dd, J=5 Hz and 8 Hz, 1H, β-lactam-H; 5.78, d, J=55 Hz, 2H, CH$_2$F; 8.07, s, 1H, CH=N; 8.27, b, 2H, NH; 9.77, d, J=8 Hz, 1H, NH.

Ex.95 (in CDCl$_3$/CD$_3$OD=1/1): 1.46, s, 3H, CH$_3$; 1.48, s, 3H, CH$_3$; 3.55 and 4.32, AB-quartet, J=18 Hz, 2H, S—CH$_2$; 3.71, AB-system, J=4 Hz and 10 Hz, 2H, N—CH$_2$; 5.18, d, J=5 Hz, 1H, β-lactam-H; 5.75, d, J=55 Hz, 2H, CH$_2$F; 5.94, d, J=5 Hz, 1H, β-lactam-H; 8.10, s, 1H, CH=N.

Ex.96 (in CDCl$_3$/CD$_3$OD=1/1): 1.46, s, 3H, CH$_3$; 1.48, s, 3H, CH$_3$; 2.84, s, 3H, N—CH$_3$; 3.56 and 4.36, AB-quartet, J=18 Hz, 2H, S—CH$_2$; 3.76, b, 2H, N—CH$_2$; 5.19, d, J=5 Hz, 1H, β-lactam-H; 5.78, d, J=55 Hz, 2H, CH$_2$F; 5.92, d, J=5 Hz, 1H, β-lactam-H; 8.06, s, 1H, CH=N.

Ex.97: 3.17, s, 3H, N—CH$_3$; 3.58, s, 3H, N—CH$_3$; 3.65 and 4.25, AB-quartet, J=18.2 Hz, 2H, S—CH$_2$; 5.28, d, J=5 Hz, 1H, β-lactam-H; 5.78, d, J=58 Hz, 2H, CH$_2$F; 5.94, dd, J=5 Hz and 8.1 Hz, 1H, β-lactam-H; 7.05, d, J=2.8 Hz, 1H, imidazole-H; 7.61, d, J=2.8 Hz, 1H, imidazole-H; 8.61, s, 1H, CH=N; 9.90, d, J=8.1 Hz, 1H, NH.

Ex.98 (in D$_2$O): 1.84, b, 2H, CH$_2$—C; 2.84, b, 2H, N—CH$_2$; 3.34, b, 2H, N—CH$_2$; 3.56 and 4.40, AB-quartet, J=18 Hz, 2H, S—CH$_2$; 3.68–4.10, m, 4H, N—CH$_2$; 5.13, d, J=5 Hz, 1H, β-lactam-H; 5.71, d, J=5 Hz, 1H, β-lactam-H; 6.64, s, 1H, thiazole-H; 7.97, s, 1H, CH=N.

Ex.99 (in D$_2$O): 3.45–3.68, m, 3H, 2H of N—CH$_2$ and 1H of S—CH$_2$; 3.70–4.10, m, 4H, N—CH$_2$; 4.40, part of AB-quartet, J=18 Hz, 1H, S—CH$_2$; 5.16, d, J=5 Hz, 1H, β-lactam-H; 5.75, d, J=5 Hz, 1H, β-lactam-H; 6.65, s, 1H, thiazole-H; 7.95, s, 1H, CH=N.

Ex.100: 1.18, t, J=7 Hz, 3H, CH$_3$; 3.15, s, 3H, N—CH$_3$; 3.42–3.68, m, 3H, 2H of N—CH$_2$ and 1H of S—CH$_2$; 3.70–4.10, m, 4H, N—CH$_2$; 4.25, part of AB-quartet, J=18 Hz, 1H, S—CH$_2$; 5.12, d, J=5 Hz, 1H, β-lactam-H, 5.69, dd, J=5 Hz and 8 Hz, 1H, β-lactam-H; 6.65, s, 1H, thiazole-H; 7.14, b, 2H, NH; 8.14, s, 1H, CH=N; 8.42, b, 1H, NH; 9.45, d, J=8 Hz, 1H, NH.

Ex.101: 3.58 and 4.47, AB-quartet, J=18 Hz, 2H, S—CH$_2$; 3.85–4.00, m, 2H, N—CH$_2$; 4.15–4.30, m, 2H, N—CH$_2$; 5.35, d, J=5 Hz, 1H, β-lactam-H; 5.81, d, J=55 Hz, 2H, CH$_2$F; 5.98, dd, J=5 Hz and 8 Hz, 1H, β-lactam-H; 7.37–7.56, m, 3H, CH-aromatic; 7.85–7.95, m, 2H, CH-aromatic; 7.99, s, 1H, aromatic-CH=N; 8.34, b, 2H, NH; 8.74, s, 1H, CH=N; 9.82, s, 1H, NH; 9.88, d, J=8 Hz, 1H, NH.

Ex.102: 3.45–3.97, m, 9H, 6H of N—CH$_2$ and 2H of O—CH$_2$ and 1H of S—CH$_2$; 4.43, part of AB-quartet, J=18 Hz, 1H, S—CH$_2$; 5.32, d, J=5 Hz; 1H, β-lactam-H; 5.8, d, J=55 Hz, 2H, CH$_2$F; 5.94, dd, J=5 Hz and 8 Hz, 1H, β-lactam-H; 8.62, s, 1H, CH=N; 8.81, s, 1H, NH; 9.86, d, 1H, NH.

Ex.103: 3.51 and 4.36, AB-quartet, J=18 Hz, 2H, S—CH$_2$; 3.71, b, 4H, N—CH$_2$; 5.29, d, J=5 Hz, 1H, β-lactam-H; 5.79, d, J=55 Hz, 2H, CH$_2$F; 5.95, dd, J=5 Hz and 8 Hz, 1H, β-lactam-H; 8.26, b, 2H, 1H of CH=N and 1H NH; 9.83, d, J=8 Hz, 1H, NH.

Ex.104: 1.90, m, 2H, CH$_2$—C; 3.33, b, 4H, N—CH$_2$; 3.50 and 4.45, AB-quartet, J=18 Hz, 2H, S—CH$_2$; 5.28, d, J=5 Hz, 1H, β-lactam-H; 5.77, d, J=55 Hz, 2H, CH$_2$F; 5.94, dd, J=5 Hz and 8 Hz, 1H, β-lactam-H; 8.30, b, 3H, 1H of CH=N and 2H of NH; 8.42, b, 2H, NH; 9.85, d, J=8 Hz, 1H, NH.

Ex.105: 3.11, b, 2H, N—CH$_2$; 3.51 and 4.39, AB-quartet, J=18 Hz, 2H, S—CH$_2$; 3.60–3.95, m, 6H, N—CH$_2$; 5.30, d, J=5 Hz, 1H, β-lactam-H; 5.77, d, J=5 Hz, 2H, CH$_2$F; 5.96, dd, 5 Hz and 8 Hz, 1H, β-lactam-H; 8.12, b, 2H, NH; 8.28, b, 2H, 1H of NH and 1H of CH=N; 8.70, b, 2H, NH; 9.82, d, J=8 Hz, 1H, NH.

Ex.106: 3.56 and 4.45, AB-quartet, J=18 Hz, 2H, S—CH$_2$; 3.75–4.25, m, 4H, N—CH$_2$; 4.30, s, 3H, CH$_3$; 5.33, d, J=5 Hz, 1H, β-lactam-H; 5.78, d, J=55 Hz, 2H, CH$_2$F; 5.98, dd, J=5 Hz and 8 Hz, 1H, β-lactam-H; 8.18, s, 1H, pyrid.—CH=N; 8.30, b, 2H, NH; 8.66 and 9.07, m, each 2H, CH-aromatic; 8.95, s, 1H, CH=N; 9.85, d, J=8 Hz, 1H, NH.

Ex.107: 3.15, s, 6H, N—CH$_3$; 3.55–3.82, m, 5H, 4H of N—CH$_2$ and 1H of S—CH$_2$; 3.95, part of AB-quartet, J=18 Hz, 1H, S—CH$_2$; 5.29, d, J=5 Hz, 1H, β-lactam-H; 5.81, d, J=55 Hz, 2H, CH$_2$F; 5.92, dd, J=5 and 8 Hz, 1H, β-lactam-H; 8.73, s, 1H, CH=N; 9.87, d, J=8 Hz, 1H, NH.

Ex.108: 1.12, t, J=7 Hz, 3H, CH$_3$; 3.42, q, J=7 Hz, 2H, N—CH$_2$; 3.51 and 4.38, AB-quartet, J=18 Hz, 2H, S—CH$_2$; 3.60–3.90, m, 4H, N—CH$_2$; 5.32, d, J=5 Hz, 1H, β-lactam-H; 5.81, d, J=55 Hz, 2H, CH$_2$F; 5.95, dd, J=5 Hz and 8 Hz, 1H, β-lactam-H; 8.31, b, 2H, NH; 8.64, s, 1H, CH=N; 8.80, b, 1H, NH; 9.86, d, J=8 Hz, 1H, NH; 12.83, s, 1H, OH.

Ex.109: 2.98, s, 3H, N—CH$_3$; 3.51 and 4.38, AB-quartet, J=18 Hz, 2H, S—CH$_2$; 3.60–3.88, m, 4H, N—CH$_2$; 5.30, d, J=5 Hz, 1H, β-lactam-H; 5.78, d, J=55 Hz, 2H, CH$_2$F; 5.94, dd, J=5 and J=8 Hz, 1H, β-lactam-H; 8.30, b, 2H, NH; 8.61, s, 1H, CH=N; 8.79, b, 1H, NH; 9.84, d, J=8 Hz, 1H, NH; 12.83, s, 1H, OH.

Ex.110: 0.87, t, J=7 Hz, 3H, CH$_3$; 1.45–1.70, m, 2H, CH$_2$—C; 3.25–3.40, m, 2H, N—CH$_2$; 3.51 and 4.39, AB-quartet, J=18 Hz, 2H, S—CH$_2$; 3.60–3.90, m, 4H, N—CH$_2$; 5.30, d, J=5 Hz, 1H, β-lactam-H; 5.79, d, J=55 Hz, 2H, CH$_2$F; 5.94, dd, J=5 Hz and 8 Hz, 1H, β-lactam-H; 8.28, b, 2H, NH; 8.61, s, 1H, CH=N; 8.77, b, 1H, NH; 9.84, d, J=8 Hz, 1H, NH; 12.76, s, 1H, OH.

Ex.111: 1.00–1.32, m, 6H, CH$_3$; 3.51 and 4.39, AB-quartet, J=18 Hz, 2H, S—CH$_2$; 3.60–3.90, m, 4H, N—CH$_2$; 4.08–4.30, m, 1H, N—CH; 5.30, d, J=5 Hz, 1H, β-lactam-H; 5.78, d, J=55 Hz, 2H, CH$_2$F; 5.94, dd, J=5 Hz and J=8 Hz, 1H, β-lactam-H; 8.32, b, 2H, NH; 8.66, s, 1H, CH=N; 8.78, b, 1H, NH; 9.86, d, J=8 Hz, 1H, NH; 12.84, s, 1H, OH.

Ex.112: 1.16, d, 12H, CH$_3$; 3.40–3.90, m, 6H, 4H of N—CH$_2$ and 2H of S—CH$_2$; 4.67, h, 2H, N—CH; 5.21, d, J=5 Hz, 1H, β-lactam-H; 5.82, d, J=55 Hz, 2H, CH$_2$F; 5.84, dd, J=5 Hz and 8 Hz, 1H, β-lactam-H; 8.26, b, 2H, NH; 8.54, s, 1H, CH=N; 9.80, d, J=8 Hz, 1H, NH.

Ex.113 (diaisostereomeric mixture): 1.27, d, J=6 Hz, 3H, CH$_3$; 3.20–3.38, m, 1H, N—CH; 3.52 and 4.37, AB-quartet, J=18 Hz, 2H, S—CH$_2$; 3.75–3.92, m, 1H, 1H of N—CH$_2$; 4.08–4.30, m, 1H, 1H of N—CH$_2$; 5.29, d, J=5 Hz, 1H, β-lactam-H; 5.79, d, J=55 Hz, 2H, CH$_2$F; 5.93, dd, J=5 Hz and 8 Hz, 1H, β-lactam-H; 8.29, b, 2H, NH; 8.38, s, 1H, CH=N; 9.84, d, J=8 Hz, 1H, NH.

Ex.114: 3.52 and 4.42, AB-quartet, J=18.2 Hz, 2H, S—CH$_2$; 3.79, s, 3H, O—CH$_3$; 3.83 and 4.02, q, 1H, J=5.5 Hz and 10.0 Hz and broad triplet, 1H, J=10.4 Hz, N—CH$_2$; 4.79, q, 1H, J=5.5 Hz and 10.4 Hz, N—CH; 5.32, d, J=5 Hz, 1H, β-lactam-H; 5.80, d, J=58 Hz, 2H, CH$_2$F; 5.94, dd, J=5 Hz and 8.2 Hz, 1H, β-lactam-H; 8.44, s, 1H, CH=N; 9.87, d, J=8.2 Hz, 1H, NH.

Ex.115: 3.4–3.9, m, 5H, 1H of NCH and 1H of NCH$_2$ and 2H of O—CH$_2$ and 1H of SCH$_2$, 4.40, m, 1H, N—CH$_2$; 4.43, part of AB-quartet, J=18 Hz, 1H, S—CH$_2$; 5.31 d, J=4.6 Hz, 1H, β-lactam-H; 5.80, d, J=55 Hz, 2H, CH$_2$F; 5.94, dd, J=4.6 Hz and 8.1 Hz, 1H, β-lactam-H; 8.40, s, 1H, CH=N; 9.86, d, J=8.1 Hz, 1H, NH.

Ex.116 (in D$_2$O): 3.11, s, 3H, N—CH$_3$; 3.28, s, 3H, N—CH$_3$; 3.58–3.71, m, 3H, 2H of N—CH$_2$ and 1H of S—CH$_2$; 3.78–3.89, m, 2H, N—CH$_2$; 3.96, s, 3H, O—CH$_3$; 3.97, part of AB-quartet, J=18 Hz, 1H, S—CH$_2$; 5.22, d, J=5 Hz, 1H, β-lactam-H; 5.76, d, J=5 Hz, 1H, β-lactam-H; 7.04, s, 1H, thiazole-H; 7.98, s, 1H, CH=N.

Ex.117 (in D$_2$O): 3.10, s, 3H, N—CH$_3$; 3.29, s, 3H, N—CH$_3$; 3.50–3.72, m, 3H, 2H of N—CH$_2$ and 1H of S—CH$_2$; 3.75–3.89, m, 2H, N—CH$_2$; 3.97, part of AB-quartet, J=18 Hz, 1H, S—CH$_2$; 5.22, d, J=5 Hz, 1H, β-lactam-H; 5.78, d, J=5 Hz, 1H, β-lactam-H; 7.02, s, 1H, thiazole-H; 7.98, s, 1H, CH=N.

Ex.118 (in DMSO-d$_6$/D$_2$O): 3.12, s, 3H, N—CH$_3$; 3.30, s, 3H, N—CH$_3$; 3.52–3.72, m, 3H, 2H of N—CH$_2$ and 1H of S—CH$_2$; 3.76–3.91, m, 2H, N—CH$_2$; 4.01, part of AB-quartet, J=18 Hz, 1H, S—CH$_2$; 5.22, d, J=5 Hz, 1H, β-lactam-H; 5.77, d, J=55 Hz, 2H, CH$_2$F; 5.83, d, J=5 Hz, 1H, β-lactam-H; 8.06, s, 1H CH=N.

Ex.119: 3.31, b, 4H, N—CH$_2$-piperazine; 3.52–4.30, m, 10H, 4H of N—CH$_2$-piperazine and 4H of N—CH$_2$-imidazole and 2H of S—CH$_2$; 5.29, d, J=5 Hz, 1H, β-lactam-H; 5.82, d, J=55 Hz, 2H, CH$_2$F; 5.90, dd, J=5 Hz and J=8 Hz, 1H, β-lactam-H; 7.98, s, 1H, CH=N; 8.30, b, 2H, NH; 9.82, d, J=8 Hz, 1H, NH.

Ex.120: (diaisostereomeric mixture): 1.15–1.60, m, 4H, CH$_2$—C; 1.62–1.85, m, 2H, CH$_2$—C; 1.88–2.22, m, 2H, CH$_2$—C; 3.20–3.40, m, 2H, N—CH; 3.52 and 4.31 bzw. 3.55 and 4.39, AB-quartet, J=18 Hz, 2H, S—CH$_2$; 5.31, d, J=5 Hz, 1H, β-lactam-H; 5.78, d, J=55 Hz, 2H, CH$_2$F; 5.94, dd, J=5 Hz and 8 Hz, 1H, β-lactam-H; 8.28, b, 2H, NH; 8.41, s, 1H, CH=N; 8.78, b, 1H, NH; 9.15, b, 1H, NH; 9.84, d, J=8 Hz, 1H, NH.

Ex. A: 3.38–3.58 and 3.60–3.80, m, 4H, N—CH$_2$.

Ex. B (in CDCl$_3$): 3.60–3.75 and 3.76–3.92, m, 4H, N—CH$_2$; 7.22–7.48, m, 4H, 3H of CH-aromatic and 1H of CH=N; 7.52–7.68, m, 2H, CH-aromatic.

Ex. C: 1.39, b, 9H, CH$_3$; 2.98–3.20 and 3.22–3.40 and 3.42–3.55 and 3.57–3.78, m, 8H, N—CH$_2$.

Ex. D (in D$_2$O): 0.80, t, J=7 Hz, 3H, CH$_3$; 1.53, hex, J=7 Hz, 2H, CH$_2$—C; 2.99, s, 3H, N—CH$_3$; 3.25, t, J=7 Hz, 2H, N—CH$_2$; 3.40–3.65, m, 4H, N—CH$_2$.

Ex. E (in D$_2$O): 0.79, t, J=7 Hz, 3H, CH$_3$; 1.52, hex, J=7 Hz, 2H, CH$_2$—C; 2.97, s, 6H, N—CH$_3$; 3.15, t, J=7 Hz, 2H, N—CH$_2$; 3.48–3.75, m, 4H, N—CH$_2$.

Ex. F (in D$_2$O): 1.68–1.90, m, 2H, CH$_2$—C; 3.08–3.32, m, 4H, N—CH$_2$; 3.42–3.70, m, 4H, N—CH$_2$.

Ex.G (in D$_2$O): 1.70–1.90, m, CH$_2$—C; 2.73, s, 6H, N—CH$_3$; 3.10–3.30, m, 4H, N—CH$_2$; 3.40–3.70, m, 4H, N—CH$_2$.

Ex. H (in D$_2$O): 1.21, d, J=7 Hz, 12H, CH$_3$; 3.70–3.96, m, 4H, N—CH$_2$; 3.98–4.18, m, 2H, N—CH.

Ex. I (in D$_2$O): 3.28–3.48, m, 4H, N—CH$_2$; 3.82–4.00, m, 4H, N—CH$_2$.

Ex. J (in CDCl$_3$): 3.12, s, 3H, N—CH$_3$; 3.57, s, 3H, N—CH$_3$; 6.95 and 6.99, AB-quartet, J=2 Hz, 2H, N—CH.

Ex. K (in D$_2$O): 3.30–3.60, m, 3H, 2H of O—CH$_2$ and 1H v N—CH$_2$; 3.78, t, J=10 Hz, 1H, N—CH$_2$; 4.14, m, 1H, N—CH.

Ex. L: 3.61, q, J=5.4 Hz and 10.3 Hz, 1H, N—CH; 3.87, s, 3H, O—CH$_3$, 4.10, t, J=10.3 Hz, 1H, N—CH$_2$; 4.56, q, J=5.4 Hz and 10.6 Hz, 1H, N—CH$_2$.

Ex. M: 3.33–3.50, m, 5H, 3H of N—CH$_3$ and 2H of N—CH$_2$; 3.66–3.78, m, 2H, N—CH$_2$.

Ex. N: 3.40–3.64 and 3.66–3.92, m, 4H, N—CH$_2$; 6.75–6.92, m, 3H, CH-aromatic; 7.15–7.40, m, 2H, CH-aromatic.

Ex. O: 2.85, d, J=5 Hz, 3H, CH$_3$; 3.40–3.56 and 3.58–3.72, m, 4H, N—CH$_2$; 8.18, d, J=5 Hz, 1H, NH.

Ex. P (in D$_2$O): 3.41–3.81, m, 16H, 8H of N—CH$_2$-piperazine and 4H of N—CH$_2$-imidazole and 4H of N—CH$_2$.

Ex. Q: 3.35–3.58, m, 4H, N—CH$_2$-imidazole; 3.60–3.72, m, 4H, 2H of N—CH$_2$ and 2H of O—CH$_2$; 7.14, b, 2H, NH$_2$.

Ex. R: 1.24, t, J=7 Hz, 3H, CH$_3$; 2.85–3.15, m, 4H, N—CH$_2$; 3.42–3.78, m, 6H, 4H of N—CH$_2$-imidazole and 2H of N—CH$_2$; 8.30, t, J=6 Hz, 1H, NH; 9.20, b, 1H, NH; 9.46, b, 2H, NH$_2$.

Ex. S (in D$_2$O): 2.87, s, 6H, CH$_3$; 3.28–3.40, m, 2H, N—CH$_2$; 3.51–3.75, m, 6H, 4H of N—CH$_2$-imidazole and 2H of N—CH$_2$.

Ex. T (in D$_2$O): 3.08–3.26, m, 2H, N—CH$_2$; 3.43–3.76, m, 6H, 4H of N—CH$_2$-imidazole and 2H of N—CH$_2$.

Ex. U: 2.68–2.91, m, 2H, N—CH$_2$; 3.30–3.76, m, 6H, 4H of N—CH$_2$-imidazole and 2H of O—CH$_2$.

Ex. V (in D$_2$O): 1.78–2.00, m, 2H, CH$_2$—C; 2.89–3.14, m, 2H, N—CH$_2$; 3.25–3.32, m, 2H, N—CH$_2$; 3.45–3.71, m, 4H, N—CH$_2$-imidazole.

Ex. W (in D$_2$O): 3.07–3.29, m, 4H, N—CH$_2$; 3.45–3.69, m, 6H, 4H of N—CH$_2$-imidazole and 2H of N—CH$_2$; 3.70–3.79, m, 2H, O—CH$_2$.

Ex. X (in D$_2$O): 3.15–3.80, m, 20H, N—CH$_2$ and O—CH$_2$.

Ex. Y (in D$_2$O): 1.20–1.50, m, 2H, CH$_2$—C; 1.72–2.00, m, 3H, CH$_2$—C and CH—C; 2.71–3.72, m, 10H, N—CH$_2$.

Ex. Z: 3.12–3.41, m, 2H, N—CH$_2$; 3.43–3.90, m, 6H, N—CH$_2$; 7.88–8.08, m, 1H, pyr.-H; 8.10–8.20, m, 1H, CH-aromatic; 8.40, b, 1H, NH; 8.50–8.68, m, 1H, CH-aromatic; 8.71–8.90, m, 1H, CH-aromatic; 9.38, b, 1H, NH.

Ex. AA: 3.28–3.72, m, 12H, N—CH$_2$ and O—CH$_2$; 8.09, t, J=6 Hz, 1H, NH, 8.86, b, 1H, NH.

Ex. AB (in D$_2$O): 3.40–3.78, m, 4H, N—CH$_2$-imidazole.

Ex. AC: 2.66–2.90, m, 4H, O—CH$_2$; 3.38–3.88, m, 8H, N—CH$_2$.

Ex. AD (in D$_2$O): 1.46–1.76, m, 4H, C—CH$_2$—C; 2.82–3.02, m, 2H, N—CH$_2$; 3.08–3.30, m, 2H, N—CH$_2$; 3.40–3.74, m, 4H, N—CH$_2$-imidazole.

Ex. AE: 3.20–3.40, m, 2H, N—CH$_2$; 3.42–3.78, m, 6H, N—CH$_2$-imidazole and O—CH$_2$; 8.14, t, J=6 Hz, 1H, NH; 8.99, b, 1H, NH.

Ex. AF (in D$_2$O): 1.13–1.38, m, 4H, CH$_2$—C; 1.40–1.68, m, 4H, CH$_2$—C; 2.78–2.98, m, 2H, N—CH$_2$; 3.02–3.22, m, 2H, N—CH$_2$; 3.40–3.68, m, 4H, N—CH$_2$-imidazole.

Ex. AG (in D$_2$O): 1.22, d, J=6 Hz, 3H, CH$_3$; 3.25–3.75, m, 7H, N—CH$_2$ and N—CH.

Ex. AH: 2.95–4.18, m, 16H, N—CH$_2$ and O—CH$_2$; 8.43, b, 1H, NH; 9.42, b, 1H, NH.

Ex. AI (in D$_2$O): 1.37, s, 6H, CH$_3$; 3.48, s, 2H, N—CH$_2$; 3.50–3.95, m, 4H, N—CH$_2$-imidazole; 7.35–7.51, m, 3H, CH-aromatic; 7.66, s, 1H, CH=N; 7.70–7.82, m, 2H, CH-aromatic.

Ex. AJ (in DMSO-d$_6$/D$_2$O): 4.00–4.22 and 4.28–4.48, m, 4H, N—CH$_2$; 4.53, s, 3H, CH$_3$; 8.14, s, 1H, CH=N; 8.48–8.62 and 8.92–9.10, m, 4H, CH-aromatic.

Ex. AK (in D$_2$O): 2.87, s, 3H, CH$_3$; 2.90–3.80, m, 12H, 8H of N—CH$_2$-piperazine and 4H of N—CH$_2$-imidazole.

Ex. AL: 0.58–0.82, m, 4H, CH$_2$—C; 2.55–2.72, m, 1H, CH—C; 3.50–3.82, m, 4H, N—CH$_2$.

Ex. AM: 1.10, t, J=7 Hz, 3H, CH$_3$; 3.27, p, J=7 Hz, 2H, N—CH$_2$; 3.42–3.78, m, 4H, N—CH$_2$; 8.30, t, J=7 Hz, 1H, NH; 9.06, b, 1H, NH.

Ex. AN: 0.86, t, J=7 Hz, 3H, CH$_3$; 1.48, h, J=7 Hz, 2H, CH$_2$; 3.16, p, J=7 Hz, 2H, N—CH$_2$; 3.40–3.72, m, 4H, N—CH$_2$; 8.30, t, J=7 Hz, 1H, NH; 9.03, b, 1H, NH.

Ex. AO (in D$_2$O): 3.08, t, J=5 Hz, 2H, N—CH$_2$; 3.33, t, J=5 Hz, 2H, N—CH$_2$; 3.42–3.71, m, 12H, 4H of N—CH$_2$ and 8H of O—CH$_2$.

Ex. AP (in D$_2$O): 1.89, p, J=7.5 Hz, 2H, CH$_2$; 2.61, s, 3H, N—CH$_3$; 3.00, t, J=7.5 H, 2H, N—CH$_2$; 3.25, t, J=7.5 Hz, 2H, N—CH$_2$; 3.42–3.72, m, 4H, N—CH$_2$.

Ex. AQ (in D$_2$O): 1.89, p, J=7.5 Hz, 2H, CH$_2$; 2.92–3.15, m, 4H, N—CH$_2$; 3.23, t, J=7.5 Hz, 2H, N—CH$_2$; 3.42–3.68, m, 4H, N—CH$_2$; 3.71, t, J=5 Hz, 2H, O—CH$_2$.

Ex. AR (in D$_2$O): 1.82–2.02, m, 2H, CH$_2$; 2.79, s, 6H, N—CH$_3$; 3.04–3.18, m, 2H, N—CH$_2$; 3.24, t, J=7 Hz, 2H, N—CH$_2$; 3.43–3.69, m 4H, N—CH$_2$.

Ex. AS (in D$_2$O): 1.84, p, J=6 Hz, 2H, CH$_2$; 3.13–3.43, m, 8H, 6H of N—CH$_2$ and 2H of O—CH$_2$; 3.68–3.84, m, 4H, N—CH$_2$.

Ex. AT (in D$_2$O): 1.85–2.12, m, 2H, CH$_2$; 2.64, s, 3H, CH$_3$; 2.95–3.12, m, 2H, N—CH$_2$; 3.30–3.42, m, 2H, N—CH$_2$; 3.50–3.78, m, 8H, 6H of N—CH$_2$ and 2H of O—CH$_2$.

Ex. AU (in D$_2$O): 1.84–2.08, m, 2H, CH$_2$; 2.98–3.18, m, 4H, N—CH$_2$; 3.30–3.42, m, 2H, N—CH$_2$; 3.48–3.82, m, 10H, 6H of N—CH$_2$ and 4H of O—CH$_2$.

Ex. AV (in D$_2$O): 1.95–2.20, m, 2H, CH$_2$; 2.88, s, 6H, N—CH$_3$; 3.12–3.28, m, 2H, N—CH$_2$; 3.38–3.50, m, 2H, N—CH$_2$; 3.58–3.83, m, 8H, 6H of N—CH$_2$ and 2H of O—CH$_2$.

Ex. AW (in D$_2$O): 2.67, s, 6H, N—CH$_3$; 3.49–3.80, m, 8H, 6H of N—CH$_2$ and 2H of O—CH$_2$.

Ex. AX (in D$_2$O): 1.69, p, J=7 Hz, 2H, CH$_2$—C; 3.19, t, J=7 Hz, 2H, N—CH$_2$; 3.40–3.64, m, 6H, 4H of N—CH$_2$ and 2H of O—CH$_2$.

Ex. AY (in D$_2$O): 3.03, s, 3H, N—CH$_3$; 3.48, t, J=5 Hz, 2H, N—CH$_2$; 3.52–3.62, m, 4H, N—CH$_2$; 3.70, t, J=5 Hz, 2H, O—CH$_2$.

Ex. AZ (in D$_2$O): 2.70–3.40, m, 4H, N—CH$_2$; 3.42–3.75, m, 4H, N—CH$_2$; 3.85–4.10, m, 1H, O—CH.

Ex. BA (in D$_2$O): 3.20–3.75, m, 16H, N—CH$_2$.

Ex. BB (in D$_2$O): 1.10, t, J=7 Hz, 3H, CH$_3$; 3.30–3.80, m, 10H, 8H of N—CH$_2$ and 2H of O—CH$_2$.

Ex. BC (in D$_2$O): 1.78–2.18, m, 4H, CH$_2$—C; 2.85–3.18, m, 6H, N—CH$_2$; 3.20–3.38, m, 2H, N—CH$_2$; 3.40–3.78, m, 4H, N—CH$_2$.

Ex. BD (in D$_2$O): 1.20–1.60, m, 4H, CH$_2$—C; 1.80–2.20, m, 4H, CH$_1$—C; 2.98–3.40, m, 2H, N—CH; 3.42–3.72, m, 4H, N—CH$_2$.

Ex. BE (in D$_2$O): 1.05, t, J=7 Hz, 3H, CH$_3$; 3.22, q, J=7 Hz, 2H, N—CH$_2$; 3.40–3.68, m, 4H, N—CH$_2$.

Ex. BF (in D$_2$O): 3.06–3.34, m, 2H, N—CH$_2$; 3.36–3.66, m, 6H, 4H of N—CH$_2$ and 2H of O—CH$_2$; 3.68–3.82, m, 1H, O—CH.

Ex. BG (in D$_2$O): 1.07, t, J=7 Hz, 3H, CH$_3$; 2.98, s, 3H, N—CH$_3$; 3.34, q, J=7 Hz, 2H, N—CH$_2$; 3.42–3.58, m, 4H, N—CH$_2$.

Ex. BH (in D$_2$O): 1.05, t, J=7 Hz, 3H, CH$_3$; 1.88–2.12, m, 2H, CH$_2$—C; 2.78, s, 6H, N—CH$_3$; 2.98–3.35, m, 4H, N—CH$_2$; 3.40–3.70, m, 6H, N—CH$_2$.

Ex. BI (in D$_2$O): 1.22, t, J=7 Hz, 3H, CH$_3$; 1.72–1.95, m, 2H, CH$_2$—C; 2.95–3.18, m, 2H, N—CH$_2$; 3.20–3.40, m, 6H, N—CH$_2$; 3.60–3.80, m, 2H, N—CH$_2$.

Ex. BJ (in D$_2$O): 1.10, t, J=7 Hz, 3H, CH$_3$; 1.25–1.60, m, 4H, CH$_2$—C; 1.82–2.20, m, 4H, CH$_2$—C; 3.00–3.20, m, 1H, N—CH; 3.29, q, J=7 Hz, 2H, N—CH$_2$; 3.42–3.68, m, 4H, N—CH$_2$; 3.85–4.10, m, 1H, N—CH.

Ex. BK (in D$_2$O): 1.25–1.60, m, 4H, CH$_2$—C; 1.85–2.20, m, 4H, CH$_2$—C; 2.96–3.25, m, 1H, N—CH; 3.30–3.40, m, 2H, N—CH$_2$; 3.50–3.78, m, 6H, 4H of N—CH$_2$ and 2H of O—CH$_2$; 4.02–422, m, 1H, N—CH.

Ex. BL (in D$_2$O): 1.65–1.95, m, 2H, CH$_2$—C; 3.05–3.38, m, 8H, N—CH$_2$; 3.40–3.82, m, 8H, N—CH$_2$.

Ex. BM (D$_2$O): 2.84, s, 3H, N—CH$_3$; 3.40–3.65, m, 4H, N—CH$_2$.

Ex. BN (in D$_2$O): 2.98, s, 3H, N—CH$_3$; 3.0, s, 3H, N—CH$_3$; 3.42–3.58, m, 4H, N—CH$_2$.

Ex. BO (in D$_2$O): 1.13, t, J=7 Hz, 3H, CH$_3$; 2.96, s, 3H, N—CH$_3$; 3.40–3.60, m, 6H, N—CH$_2$.

Ex. BP (D$_2$O): 1.25–1.60, m, 4H, CH$_2$—C; 1.85–2.18, m, 4H, CH$_2$—C; 2.93, s, 3H, N—CH$_3$; 3.02–3.25, m, 1H, N—CH; 3.40–3.68, m, 4H, N—CH$_2$; 3.88–4.10, m, 1H, N—CH.

Ex. BQ (D$_2$O): 2.95, s, 3H, N—CH$_3$; 3.42–3.70, m, 8H, 6H of N—CH$_2$ and 2H of O—CH$_2$.

Ex. BR (D$_2$O): 3.25–3.82, m, 12H, 8H of N—CH$_2$ and 4H of O—CH$_2$.

Ex. BS (D$_2$O): 1.22, t, J=7 Hz, 6H, CH$_3$; 3.10–3.28, m, 4H, N—CH$_2$; 3.30–3.42, m, 2H, N—CH$_2$; 3.50–3.75, m, 6H, N—CH$_2$.

Ex. BT (in D$_2$O): 1.88–2.08, m, 2H, CH$_2$—C; 2.83, s, 6H, N—CH$_3$; 3.05–3.20, m, 2H, N—CH$_2$; 3.25–3.38, m, 2H, N—CH$_2$; 3.46–3.70, m, 4H, N—CH$_2$.

Ex. BU (in D$_2$O): 1.20, t, J=7 Hz, 6H, CH$_3$; 3.22, q, J=7 Hz, 4H, N—CH$_2$; 3.26–3.38, m, 2H, N—CH$_2$; 3.48–3.74, m, 6, N—CH$_2$.

Ex. BV (in D$_2$O): 0.24, t, J=7 Hz, 3H, CH$_3$; 3.07, s, 3H, N—CH$_3$; 3.12–3.92, m, 12H, N—CH$_2$.

Ex. BW (in D$_2$O): 2.87, s, 6H, N—CH$_3$; 3.30–3.48, m, 2H, N—CH$_2$; 3.50–3.78, m, 6H, N—CH$_2$.

Ex. BX (in D$_2$O): 3.55–3.82, m, 4H, N—CH$_2$; 5.00, s, 2H, O—CH$_2$; 7.10, s, 1H, CH; 7.99, s, 1H, CH.

Ex. BY (in D$_2$O): 1.10–1.54, m, 4H, CH$_2$—C; 1.56–1.84, m, 2H, CH$_2$—C; 1.86–2.18, m, 2H, CH$_2$C; 3.10–3.46, m, 2H, N—CH; 3.48–3.70, m, 4H, N—CH$_2$.

Ex. BZ (in D$_2$O): 0.79, t, J=7 Hz, 3H, CH$_3$; 1.51, hex, J=7 Hz, 2H, CH$_2$—C; 3.15, t, J=7 Hz, 2H, N—CH$_2$; 340–3.70, m, 4H, N—CH$_2$.

Ex. CA (in D$_2$O): 1.11, d, J=7 Hz, 6H, CH$_3$; 3.40–3.62, m, 4H, N—CH$_2$; 3.72–3.92, m, 1H, N—CH.

Ex. CB (in D$_2$O): 122–2.00, m, 6H, CH$_2$—C; 2.80–3.08, m, 2H, N—CH$_2$; 3.20–3.82, m, 10H, N—CH$_2$.

Ex. CC (in D$_2$O): 0.80, t, J=7 Hz, 3H, CH$_3$; 1.10–1.38, m, 2H, CH$_2$—C; 1.40–1.58, m, 2H, CH$_2$—C; 3.00, s, 3H, N—CH$_3$; 3.20–3.38, m, 2H, N—CH$_2$; 3.40–3.68, m, 4H, N—CH$_2$.

Ex. CD (in D$_2$O): 0.80, t, J=7 H, 3H, CH$_3$; 1.08–1.32, m, 2H, CH$_2$—C; 1.36–1.62, m, 2H, CH$_2$—C; 3.08–3.30, m, 2H, N—CH$_2$; 3.40–3.70, m, 4H, N—CH$_2$.

Ex. CE (in D$_2$O): 1.10–1.90, m, 6H, CH$_2$—C; 2.78–3.04, m, 5H, 2H of N—CH$_2$ and 3H of N—CH$_3$; 3.20–3.90, m, 10H, N—CH$_2$.

Ex. CF (in D$_2$O): 1.75–2.22, m, 4H, CH$_2$—C; 292–3.18, m, 2H, N—CH$_2$; 3.32–3.48, m, 2H, N—CH$_2$; 3.48–3.78, m, 8H, N—CH$_2$.

Ex. CG (D$_2$O): 3.48–3.72, m, 4H, N—CH$_2$; 4.11, s, 2H, CH$_2$.

Ex. CH (D$_2$O): 0.79, t, J=7 Hz, 3H, CH$_3$; 1.08–1.40, m, 4H, CH$_2$—C; 1.42–1.68, m, 2H, CH$_2$—C; 3.10–3.32, m, 2H, N—CH$_2$; 3.40–3.70, m, 4H, N—CH$_2$.

Ex. CI (D$_2$O): 0.75, t, J=7 Hz, 3H, CH$_3$; 1.08–1.32, m, 6H, CH$_2$—C; 1.48–1.60, m, 2H, CH$_2$—C; 3.10–3.25, m, 2H, N—CH$_2$; 3.40–3.68, m, 4H, N—CH$_2$.

Ex. CJ (D$_2$O): 0.90, t, J=7 Hz, 3H, CH$_3$; 1.20–1.48, m, 8H, CH$_2$—C; 1.52–1.75, m, 2H, CH$_2$—C; 3.25–3.40, m, 2H, N—CH$_2$; 3.52–3.80, m, 4H, N—CH$_2$.

Ex. CK (D$_2$O): 1.80–2.02, m, 2H, CH$_2$—C; 3.10–3.38, m, 4H, N—CH$_2$; 3.40–3.65, m, 4H, N—CH$_2$.

Ex. CL (in D$_2$O): 1.09, t, J=7 Hz, 3H, CH$_3$; 2.98, s, 6H, N—CH$_3$; 3.26, q, J=7 Hz, 2H, N—CH$_2$; 3.48–3.75, m, 4H, NCH$_2$.

Ex. CM (in D$_2$O): 2.90, s, 3H, N—CH$_3$; 2.99, s, 6H, N—CH$_3$; 3.45–3.75, m, 4H, N—CH$_2$.

Ex. CN (in D$_2$O): 1.00–1.22, m, 6H, CH$_3$; 2.94, s, 3H, N—CH$_3$; 3.12–3.45, m, 4H, N—CH$_2$; 3.50–3.72, m, 4H, N—CH$_2$.

Ex. CO (in D$_2$O): 3.1, s, 3H, N—CH$_3$; 3.20–3.42, m, 4H, N—CH$_2$; 3.75–4.02, m, 4H, N—CH$_2$.

Ex. CP (in D$_2$O): 1.72–2.02, m, 2H, CH$_2$—C; 2.95–3.30, m, 7H, 3H of N—CH$_3$ and 4H of N—CH$_2$; 3.32–3.70, m, 4H, N—CH$_2$.

Ex. CQ (in D$_2$O): 1.17, d, J=6 Hz, 3H, CH$_3$; 2.75, s, 3H, N—CH$_3$; 3.05–3.28, m, 1H, N—CH; 3.60–4.10, m, 2H, N—CH$_2$.

Ex. CR (in D$_2$O): 1.17, d, J=6 Hz, 3H, CH$_3$; 3.12–3.30, m, 1H, N—CH; 3.68–4.05, m, 2H, N—CH$_2$.

Ex. CS (in D$_2$O): 1.2, d, J=6 Hz, 3H, CH$_3$; 1.72–2.12, m, 2H CH$_2$—C; 2.88–3.10, m, 2H, N—CH$_2$; 3.12–3.45, m, 3H, 2H of N—CH$_2$ and 1H of N—CH; 3.68–4.15, m, 2H, N—CH$_2$.

Ex. CT (in CDCl$_3$/CD$_3$OD=1/1): 1.40, s, 6H, CH$_3$; 2.90, s, 3H, N—CH$_3$; 3.58, s, 2H, N—CH$_2$.

Ex. CU (in CDCl$_3$/CD$_3$OD=1/1): 1.40, s, 6H, CH$_3$; 3.54, s, 2H, N—CH$_2$.

Ex. CV: 0.84, t, J=7 Hz, 3H, CH$_3$; 1.49, hex, J=7 Hz, 2H, CH$_2$—C; 3.16, t, J=7 Hz, 2H, N—CH$_2$; 3.42–3.72, m, 4H, N—CH$_2$.

Ex. CW (in D$_2$O): 1.14, d, J=7 Hz, 6H, CH$_3$; 3.50–3.92, m, 5H, 4H of N—CH$_2$ and 1H of N—CH.

Ex. CX: 1.12, d, 12H, CH$_3$; 3.50, b, 4H, N—CH$_2$; 4.88, h, 2H, N—CH.

Ex. CY: 3.17, b, 4H, N—CH$_2$-piperazine; 3.40–3.58 and 3.68–3.88, m, 4H, N—CH$_2$-imidazole; 3.98, b, 4H, N—CH$_2$; 9.16, b, 1H, NH; 10.01, b, 2H, NH$_2$.

Ex. CZ (in D$_2$O): 3.05, s, 3H, N—CH$_3$; 3.20, s, 3H, N—CH$_3$; 3.45–3.54, m, 2H, N—CH$_2$; 3.66–3.76, m, 2H, N—CH$_2$.

Ex. DB (in CDCl$_3$): 1.26, t, J=7 Hz, 3H, CH$_3$; 3.70–4.00, m, 6H, N—CH$_2$.

What is claimed is:
1. A compound of formula

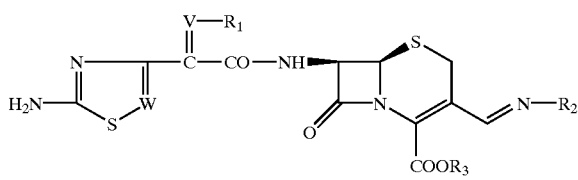

I wherein

W denotes CH or N,
V denotes CH or NO,
R$_1$ denotes hydrogen, (C$_{1-12}$)acyl, carboxyl or alkyl,
R$_3$ denotes hydrogen or an ester moiety or a cation,
R$_2$ denotes a group of formula

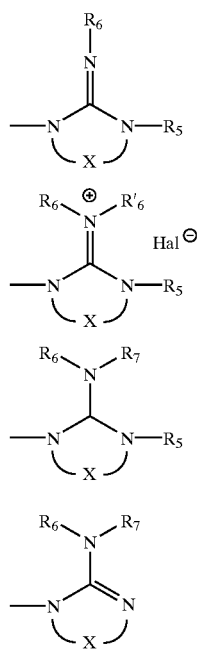

a)

a')

b)

c)

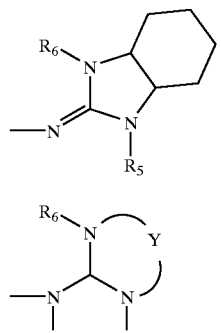

d')

e)

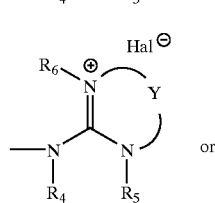

e')

or

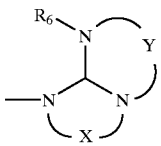

g)

wherein
X and Y independently of each other each denote (C$_{2-5}$)alkylene, or
(C$_{2-5}$)alkenylene wherein one —C=C— double bond is present, or, in case of at least C$_4$-alkenylene, wherein two —C=C— double bonds are present,
R$_4$ denotes hydrogen or alkyl,
R$_5$ denotes hydrogen, alkyl, or aminoiminomethyl,
R$_6$ denotes hydrogen, alkyl, cycloalkyl, amino, hydroxy, alkoxy, unsaturated or saturated heterocyclyl having 5 or 6 ring members and 1 or 2 hetero atoms and being unsubstituted or substituted by alkyl, aryl, alkoxy, halogen, hydroxy, carboxyl, —SO$_3$H, C$_{(1-12)}$-acyl, amino, guanidino, oxo, thiono, mercapto, alkylthio, arylthio, imino or alkylimino, or R$_6$ denotes a group of formula —N=CHR$_8$, wherein
R$_8$ denotes alkyl, aryl or unsaturated or saturated heterocyclyl having 5 or 6 ring members and 1 or 2 hetero atoms and being unsubstituted or substituted by alkyl, aryl, alkoxy, halogen, hydroxy, carboxyl, —SO$_3$H, C$_{(1-12)}$-acyl, amino, guanidino, oxo, thiono, mercapto, alkylthio, arylthio, imino or alkylimino, or
R$_5$ and R$_6$ together with the nitrogen atoms to which they are attached denote unsaturated or saturated heterocyclyl having 5 or 6 ring members and 1 or 2 hetero atoms and being unsubstituted or substituted by alkyl, aryl, alkoxy, halogen, hydroxy, carboxyl, —SO$_3$H, C$_{(1-12)}$-acyl, amino, guanidino, oxo, thiono, mercapto, alkylthio, arylthio, imino or alkylimino,
R'$_6$ denotes alkyl,
R$_7$ denotes hydrogen, or
R$_6$ and R$_7$ together with the nitrogen atom to which they are attached form unsaturated or saturated heterocyclyl having 5 or 7 ring members and 1 or 2 hetero atoms and being unsubstituted or substituted by alkyl, aryl, alkoxy, halogen, hydroxy, carboxyl, —SO$_3$H, C$_{(1-12)}$-acyl, amino, guanidino, oxo, thiono, mercapto, alkylthio, arylthio, imino or alkylimino.

2. A compound of formula

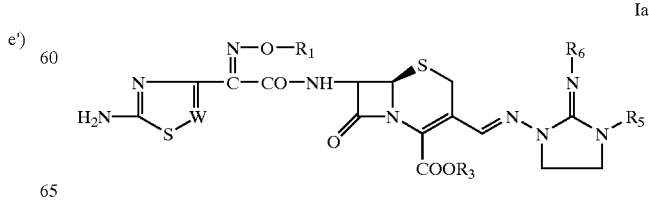

Ia wherein W, R$_1$, R$_3$, R$_5$ and R$_6$ are as defined in claim 1.

3. A compound of formula

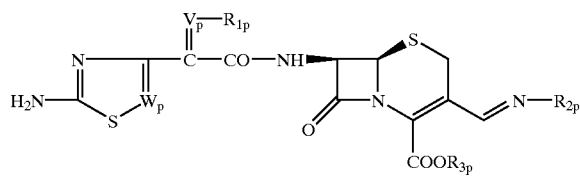

Ip wherein $W_p$ denotes CH or N, $V_p$ denotes =CH— or =N—O—, $R_{1p}$ denotes hydrogen, $C_{(1-12)}$-acyl, carboxyl, unsubstituted alkyl, or alkyl substituted by halogen or carboxyl, $R_{3p}$ denotes hydrogen, an ester forming group or a cation, $R_{2p}$ denotes a group of formula

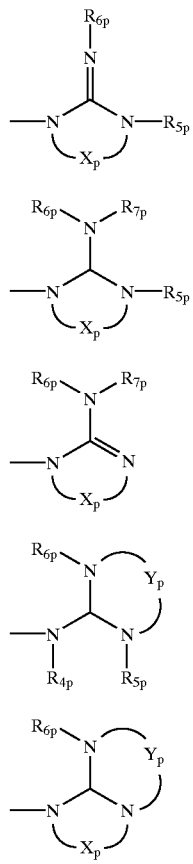

a)

b)

c)

e)

g)

wherein $X_p$ and $Y_p$ are the same or different and each denote a —$(CH_2)_n$-group, wherein n denote a number from 2 to 5, and optionally two $CH_2$-groups are replaced by a —CH=CH— group and optionally one or more hydrogen atoms are replaced by halogen, alkyl, cycloalkyl, hydroxyalkyl, aminoalkyl, carboxyl or ethoxycarbonyl, $R_{4p}$ denotes hydrogen, alkyl or hydroxyalkyl, $R_{5p}$ denotes hydrogen, alkyl, (poly)hydroxyalkyl or aminoalkyl, wherein optionally the alkyl groups are additionally substituted by —COOH, —$SO_3H$, or —$OPO_3H_2$, $R_{6p}$ denotes hydrogen, alkyl, hydroxyalkyl, aminoalkyl, amino, hydroxy, alkoxyalkyl, cycloalkyl, a group N=$CHR_{8p}$, wherein $R_{8p}$ denotes aryl or heteroaryl, or a group —$NR_{9p}R_{10p}$, wherein $R_{9p}$ and $R_{10p}$ are the same or different and each denote hydrogen, alkyl, hydroxyalkyl or aryl or denote together with the nitrogen atom a saturated, unsubstituted heterocycle with 5 or 6 ring members with one or two nitrogen and/or oxygen atoms, and $R_{7p}$ denotes hydrogen, or $R_{7p}$ and $R_{6p}$ denote together with the nitrogen atom a heterocycle with 5 to 7 ring members containing one or two nitrogen and/or oxygen atoms, in free form, or, where such forms exist, in the form of salts or hydrates thereof.

4. A process for the production of a compound of formula I as defined in claim 1, comprising reacting a compound of formula

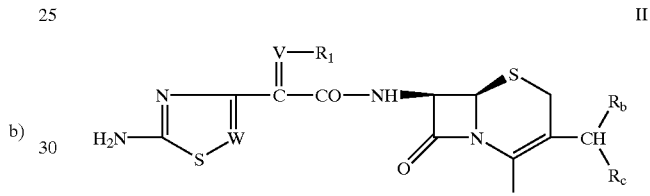

II wherein W, V and $R_1$ are as defined in claim 1 and either

α) $R_b$ denotes hydroxy and $R_c$ and $R_d$ together denote a bond, or

β) $R_d$ denotes hydrogen, a cation, an ester forming group or a silyl group, and $R_b$ and $R_c$ together denote the oxo group, in free form or in the form of an acid addition salt thereof, with an amine of formula $R_2$—$NH_2$  III wherein $R_2$ is as defined in claim 1.

5. A pharmaceutical compositions comprising a compound of formula I as defined in claim 1 in pharmaceutically acceptable salt form or free form in association with at least one pharmaceutical carrier or diluent.

6. A method of treatment of bacterial diseases which comprises administering to a subject in need of such treatment an effective amount of a compound of formula I as defined in claim 1.

7. The method of claim 6 characterized in that bacterial diseases are caused by a bacteria genus selected from the group consisting of Pseudomonas, Escherichia, Enterobacter, Klebsiella, Moraxella, Enterococcus, Streptococcus, Staphylococcus.

8. 7-{[(5-Amino-1,2,4-thiadiazole-3-yl)-(Z)-(fluoromethoxyimino)acetyl]amino}-3-{[(3-ethyl-2-methylimino-imidazolidine-1-yl)imino]methyl}-3-cephem-4-carboxylic acid.

* * * * *